(12) United States Patent
Sanderson et al.

(10) Patent No.: US 7,919,251 B2
(45) Date of Patent: Apr. 5, 2011

(54) NON-THIOPURINE METHYLTRANSFERASE RELATED EFFECTS IN 6-MERCAPTOPURINE THERAPY

(75) Inventors: Jeremy D. Sanderson, London (GB); Anthony M. Marinaki, London (GB); Melissa A. Smith, Hampshire (GB)

(73) Assignee: Guy's and St. Thomas' NHS Foundation Trust, London (GB)

( * ) Notice: Subject to any disclaimer, the term of this patent is extended or adjusted under 35 U.S.C. 154(b) by 317 days.

(21) Appl. No.: 12/248,866

(22) Filed: Oct. 9, 2008

(65) Prior Publication Data
US 2009/0203004 A1 Aug. 13, 2009

Related U.S. Application Data

(60) Provisional application No. 60/979,787, filed on Oct. 12, 2007.

(51) Int. Cl.
*C07H 21/04* (2006.01)
*C12Q 1/68* (2006.01)

(52) U.S. Cl. ......... 435/6; 435/91.1; 435/91.2; 536/23.1; 536/24.3

(58) Field of Classification Search .................. None
See application file for complete search history.

(56) References Cited

U.S. PATENT DOCUMENTS

| 5,691,343 | A | 11/1997 | Sandborn |
| 6,987,097 | B2 | 1/2006 | Seidman et al. |
| 2005/0202483 | A1 | 9/2005 | Sanderson et al. |
| 2005/0227917 | A1 | 10/2005 | Williams et al. |
| 2007/0031846 | A1 | 2/2007 | Cargill et al. |

FOREIGN PATENT DOCUMENTS

| WO | WO 2005/078125 A2 | 8/2005 |
| WO | WO 2007/073478 A2 | 6/2007 |

OTHER PUBLICATIONS

Smith et al. Aliment Pharmacol Ther, vol. 30, pp. 375-384, 2009.*
Rashidi et al, Drug Metabolism and Pharmacokinetics, vol. 22, No. 4, pp. 299-306, Aug. 2007.*
Genbank dbSNP rs5575465, Sep. 18, 2007.*
Dubinsky, et al.; 6-MP Metabolite Profiles Provide a Biochemical Explanation for 6-MP Resistance in Patients with Inflammatory Bowel Disease; Gastroenterology 2002:122:904-915.
Lennard, et al.; Pharmacogenetics of acute azathioprine toxicity: Relationship to thiopurine methyltransferase genetic polymorphism; Clin Pharmacol Ther; Aug. 1989; 46:149-54.
Mardini, et al.; Utility of Measuring 6-Methylmercaptopurine and 6-Thioguanine Nucleotide Levels in Managing Inflammatory Bowel Disease Patients Treated with 6-Mercaptopurine in a Clinical Practice Setting; J Clin Gastroenterol 2003: 36(5):390-395.
Papadakis; Optimizing the Therapeutic Potential of Azathioprine/6-Mercaptopurine in the Treatment of Inflammatory Bowel Disease; J Clin Gastroenterol 2003:36(5):379-385.
Present, et al.; 6-Mercaptopurine in the Management of Inflammatory Bowel Disease: Short and Long-Term Toxicity; Annals of Internal Medicine 1989: 111:641-649.
Valik et al.; Hereditary Disorders Of Purine and Pyrimidine Metabolism: Identification Of Their Biochemical Phenotypes In the Clinical Laboratory; Mayo Clin Proc; Aug. 1997, 72:719-725.
Hawwa et al. "Pharmacogenomic studies of the anticancer and immunosuppressive thiopurines mercaptopurine and azathioprine," British Journal of Clinical Pharmacology, vol. 66, No. 4, pp. 517-528, 2008.
Katsanos et al. "Analysis of genetic variants in non-TPMT genes to explain bone marrow toxicity during azathioprine therapy in inflammatory bowel disease," XP002516154, Digestive Disease Week Meeting/109th Annual Meeting of the American-Gastroenterological-Association, 2008, vol. 134, No. 4, Suppl. 1, Database accession No. PREV200800414803, Database BIOSIS [Online] Biosciences Information Service [Abstract].
Katsanos et al. "Azathioprine/6-mercaptopurine toxicity: The role of the TPMT gene," Annals of Gastroenterology, 2007, vol. 20, No. 4, pp. 251-264.
Rashidi et al. "In Vitro Study of 6-mercaptopurine Oxidation Catalysed by Aldehyde Oxidase and Xathine Oxidase," Drug Metab. Pharmacokinet. 2007, vol. 22, No. 4, pp. 299-306.
Smith et al. "Common polymorphism in the aldehyd oxidase gene is a marker of non-response to azathioprine therapy in inflammatory bowel disease," XP002516153, Annual General Meeting of the British-Society-of-Gastroenterology, 2008, vol. 57, Suppl. 1. p. A36, Database Accession No. PREV200800333950, Database BIOSIS [Online] Biosciences Information Service [Abstract].
Smith et al. "Seeking pharmacogenetic loci which explain non-thiopurine methyltransferase related side effects in patients taking azathioprine for inflammatory bowel disease," XP002516152, Annual General Meeting of the British-Scoiety-of-Gastroenerology, 2008, vol. 57, Suppl. 1, p. A148, Database Accession No. PREV200800334244, Database BIOSIS [Online] Biosciences Information Service [Abstract].

* cited by examiner

*Primary Examiner* — Jeanine A Goldberg
(74) *Attorney, Agent, or Firm* — Kilpatrick, Townsend & Stockton LLP

(57) ABSTRACT

The present invention provides methods for predicting tolerance associated with 6-mercaptopurine drug treatment of an immune-mediated gastrointestinal disorder such as inflammatory bowel disease. In particular, the present invention provides methods for predicting a patient's risk of an adverse drug reaction (or tolerance) to a 6-mercaptopurine drug by genotyping a patient at a polymorphic site in at least one gene selected from the group consisting of a xanthine dehydrogenase (XDH) gene, molybdenum cofactor sulfurase (MOCOS) gene, and aldehyde oxidase (AOX) gene. The present invention further provides methods for optimizing therapeutic efficacy in a patient receiving a 6-mercaptopurine drug by determining whether the patient should be given an alternative drug based on the presence or absence of a polymorphism in at least one of the XDH, MOCOS, and AOX genes.

11 Claims, 1 Drawing Sheet

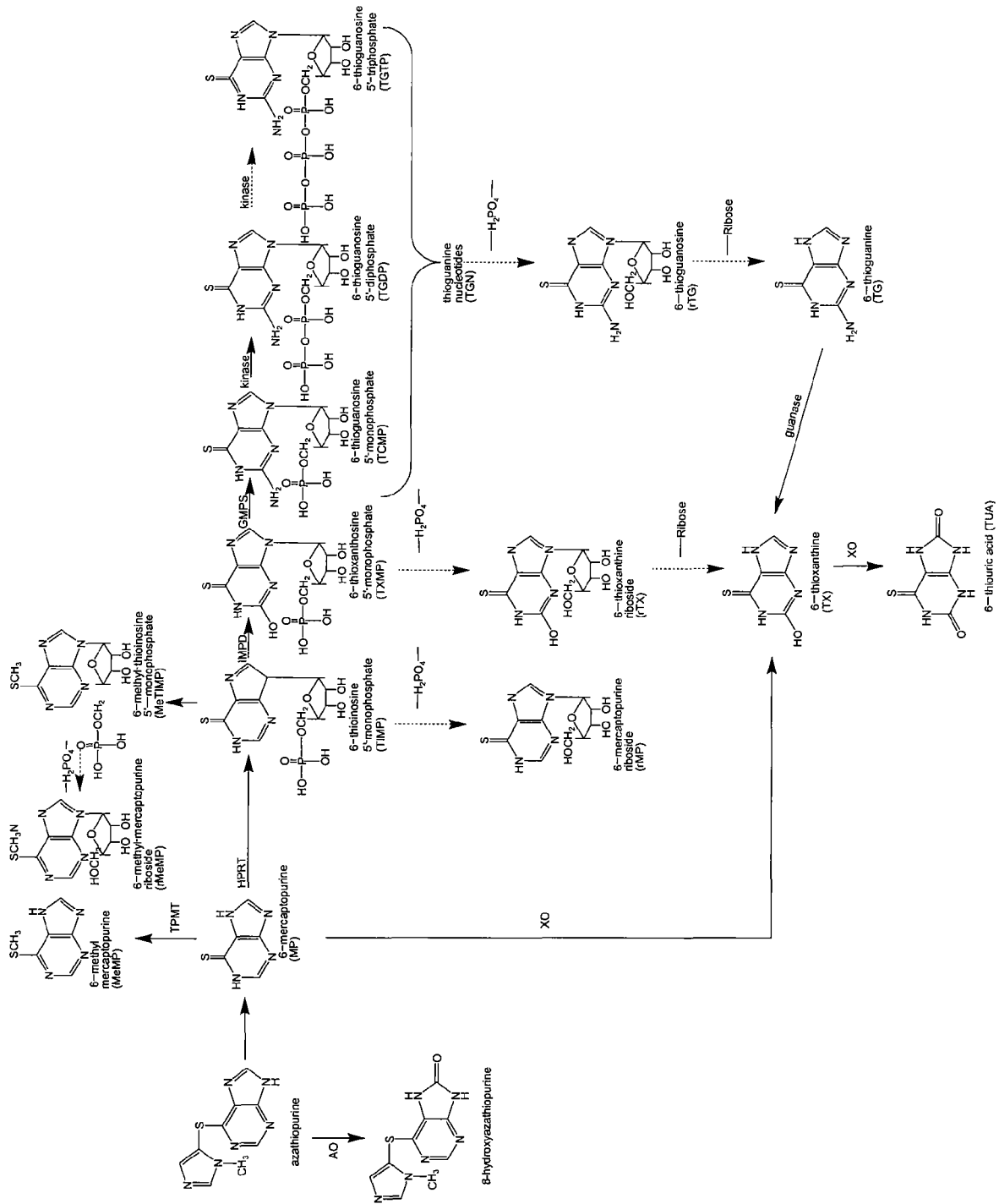

NON-THIOPURINE METHYLTRANSFERASE RELATED EFFECTS IN 6-MERCAPTOPURINE THERAPY

CROSS-REFERENCES TO RELATED APPLICATIONS

This application claims priority to U.S. Provisional Patent Application No. 60/979,787, filed Oct. 12, 2007, the teachings of which are incorporated herein by reference in their entirety for all purposes.

FIELD OF THE INVENTION

The present invention provides a method for optimizing therapeutic efficacy and predicting tolerance of 6-mercaptopurine (6-MP) drug treatment, especially in an immune-mediated gastrointestinal disorder.

BACKGROUND OF THE INVENTION

Mercaptopurine (6-MP or 6-thiopurine) and azathioprine [6-(1-methyl-4-nitro-5-imidazolylthio)purine] are cytotoxic drugs that are effective in the treatment of ulcerative colitis and Crohn's disease (see, Present et al., *Annals of Internal Medicine* 111:641-649 (1989)). The prodrug azathioprine (AZA) is rapidly converted to 6-mercaptopurine through non-enzymatic, nucleophilic attack by sulfhydryl-containing compounds in the circulation. 6-MP and AZA, which are forms of the same drug and metabolic precursors of the active components, are acted upon by at least three competing enzymatic pathways. As shown in FIG. 1, several major enzyme pathways are involved. Xanthine oxidase (XO) converts 6-mercaptopurine to 6-thiouric acid. Hypoxanthine phosphoribosyl transferase (HPRT) converts 6-mercaptopurine to 6-thioinosine-5'-monophosphate, which is a precursor to 6-thioguanine nucleotides. Thiopurine methyltransferase (TPMT) catalyzes the S-methylation of 6-mercaptopurine to methylmercaptopurine (6-MMP). Thus, 6-mercaptopurine is enzymatically converted to various metabolites, including 6-thioguanine (6-TG) and 6-thioguanine nucleotides, which are the presumptive active metabolites mediating the effects of azathioprine/6-mercaptopurine drug therapy.

The interplay of the pathways described above is genetically determined and creates a highly individualized response to azathioprine/6-mercaptopurine drug therapy. The population frequency distribution of TPMT enzyme is trimodal, with the majority of individuals (89%) having high activity, 11% having intermediate activity, and about 1 in 300 (0.33%) having undetectable activity (see, Weinshilboum and Sladek, *Amer. J. Human Genetics* 32:651-662 (1980)). Such a trimodal relationship has been confirmed by direct measurements of TPMT enzyme activity by the Kroplin HPLC assay method (see, Kroplin et al., *Eur. J. Clin. Pharmacol.*, 54 265-271 (1998)). In contrast to variation in TPMT activity, there is very little inter-individual variation in XO activity and only limited data on HPRT activity (see, Lennard, *Eur. J. Clin. Pharm.*, 43:329-339 (1992)).

In certain populations, very high levels of methylated metabolites (e.g., 6-methyl-mercaptopurine (6-MMP)) are seen in red blood cells with normal thiopurine methyltransferase (TPMT) activity. This phenomenon has gone unexplained. There is contradictory evidence in the literature that high levels of methylated metabolites are associated with hepatotoxicity. Interestingly, when these patients are treated with a combination of allopurinol and azathioprine, methylated metabolites return to normal and thioguanine nucleotide levels can be pushed into the therapeutic range.

In view of the foregoing, there is a need in the art to understand the genetic interplay of the pathways described above as to create a highly individualized dose of a 6-mercaptopurine producing drug. The present invention satisfies this and other needs.

BRIEF SUMMARY OF THE INVENTION

The present invention provides methods for predicting a patient's risk of an adverse drug reaction (or tolerance) to a 6-mercaptopurine drug (e.g., AZA, 6-MP, or metabolites thereof) by genotyping a patient at a polymorphic site in at least one gene selected from the group consisting of a xanthine dehydrogenase (XDH) gene, molybdenum cofactor sulfurase (MOCOS) gene, and aldehyde oxidase (AOX) gene. The present invention further provides methods for optimizing therapeutic efficacy in a patient receiving a 6-mercaptopurine drug by determining whether the patient should be given an alternative drug based on the presence or absence of a polymorphism in at least one gene selected from the group consisting of a xanthine dehydrogenase (XDH) gene, molybdenum cofactor sulfurase (MOCOS) gene, and aldehyde oxidase (AOX) gene.

As such, the present invention provides a method for predicting clinical response or tolerance of a drug providing 6-mercaptopurine in an individual in need thereof, the method comprising:
(a) genotyping the individual at a polymorphic site in at least one gene selected from the group consisting of a xanthine dehydrogenase (XDH) gene, molybdenum cofactor sulfurase (MOCOS) gene, aldehyde oxidase (AOX) gene, and a combination thereof; and
(b) determining the presence or absence of a variant allele at the polymorphic site, wherein the presence of the variant allele at the polymorphic site is indicative of clinical response or tolerance to the drug.

The methods described herein are useful in diseases or disorders such as an immune-mediated gastrointestinal disorder, an autoimmune disease, and graft versus host disease. The methods are especially useful in an immune-mediated gastrointestinal disorder such as inflammatory bowel disease, especially Crohn's disease.

In another embodiment, the present invention provides a method for predicting response to a drug providing 6-mercaptopurine in an individual in need thereof, the method comprising:
genotyping an aldehyde oxidase (AOX) gene of the individual for the presence or absence of a 3404 A>G (exon 30) variant allele, wherein the presence of the variant allele indicates that the individual should be given an alternative drug.

In yet another embodiment, the present invention provides a method for predicting tolerance of a drug providing 6-mercaptopurine in an individual in need thereof, the method comprising:
genotyping a xanthine dehydrogenase (XDH) gene of the individual for the presence or absence of a 837C>T (exon 10) variant allele, wherein the presence of the variant allele indicates that the individual is protected against side-effects to the drug.

Other objects, features, and advantages of the present invention will be apparent to one of skill in the art from the following detailed description and figure, which follows.

BRIEF DESCRIPTION OF THE DRAWINGS

FIG. 1 shows the metabolism of azathioprine and 6-mercaptopurine. 6-mercaptopurine metabolic pathways are indicated by solid arrows; dashed arrows indicate putative products of dephosphorylation to nucleotides and further catabolism to nucleobases. HPRT, hypoxanthine phosphoribosyltransferase; TMPT, thiopurine methyltransferase; XO, xanthine oxidase; IMPD, inosine monophosphate dehydrogenase; GMPS, guanosine monophosphate synthetase.

DETAILED DESCRIPTION OF THE INVENTION

I. Definitions

As used herein, the following terms have the meanings ascribed to them unless specified otherwise.

As used herein, the term "6-mercaptopurine drug" or "6-MP drug" includes any drug that can be metabolized to an active 6-mercaptopurine metabolite that has therapeutic efficacy such as 6-TG. Exemplary 6-mercaptopurine drugs as defined herein include 6-mercaptopurine (6-MP) and azathioprine (AZA). As illustrated in FIG. 1, both 6-MP and AZA can be metabolized to 6-mercaptopurine metabolites such as the exemplary 6-mercaptopurine metabolites shown, including 6-thioguanine (6-TG), 6-methyl-mercaptopurine (6-MMP), and 6-thiouric acid (see, Lennard, *Eur. J. Clin. Pharmacol.* 43:329 339 (1992)).

Other 6-MP drugs include, for example, 6-methylmercaptopurine riboside and 6-TG (see, Loo et al., *Clin. Pharmacol. Ther.* 9:180 194 (1968); O'Dwyer et al., *J. Natl. Cancer Inst.* 83:1235 1240 (1991); Erb et al., *Cancer Chemother. Pharmacol.* 42:266 272 (1998); Lancaster et al., *Br. J. Haematol.* 102:439 443 (1998); Ingle et al., *Am. J. Clin. Oncol.* 20:69 72 (1997); Evans and Relling, *Leuk. Res.* 18:811 814 (1994)). 6-TG is a particularly useful 6-MP drug in patients having high TPMT activity. Patients exhibiting high TPMT activity are expected to more easily convert 6-MP drugs such as 6-MP and AZA to 6-MMP (see, FIG. 1). As disclosed herein, high levels of 6-MMP are associated with hepatotoxicity. Therefore, patients with high TPMT activity can be more susceptible to toxic effects of 6-MP drug therapy. By administering 6-TG, which is an active 6-MP metabolite associated with therapeutic efficacy, the toxicity that can be associated with conversion of 6-MP to 6-MMP is bypassed.

As used herein, the term "6-thioguanine" or "6-TG" includes 6-thioguanine or analogues thereof, including molecules having the same base structure, for example, 6-thioguanine ribonucleoside, 6-thioguanine ribonucleotide mono-, di- and tri-phosphate, 6-thioguanine deoxyribonucleoside and 6-thioguanine deoxyribonucleotide mono, di, and triphosphate. The term "6-TG" also includes derivatives of 6-thioguanine, including chemical modifications of 6-TG, so long as the structure of the 6-TG base is preserved.

As used herein, the term "6-methyl-mercaptopurine" or "6-MMP" includes 6-methyl-mercaptopurine or analogues thereof, including analogues having the same base structure, for example, 6-methyl-mercaptopurine ribonucleoside, 6-methyl-mercaptopurine ribonucleotide mono-, di-, and tri-phosphate, 6-methyl-mercaptopurine deoxyribonucleoside, and 6-methyl-mercaptopurine deoxyribonucleotide mono-, di- and tri-phosphate. The term "6-MMP" also includes derivatives of 6-methyl-mercaptopurine, including chemical modifications of 6-MMP, so long as the structure of the 6-MMP base is preserved.

As used herein, the term "6-mercaptopurine metabolite" includes a product derived from 6-mercaptopurine in a biological system. Exemplary 6-mercaptopurine metabolites are shown in FIG. 1 and include 6-thioguanine (6-TG), 6-methyl-mercaptopurine (6-MMP) and 6-thiouric acid and analogues thereof. For example, 6-MP metabolites include 6-TG bases such as 6-TG, 6-thioguanosine mono-, di- and tri-phosphate; 6-MMP bases such as 6-methyl-mercaptopurine and 6-methyl-thioinosine monophosphate; 6-thioxanthosine (6-TX) bases such as 6-thioxanthosine mono-phosphate; 6-thiouric acid (6-TUA); and 6-MP bases such as 6-mercaptopurine and 6-thioinosine monophosphate. The immunosuppressive properties of 6-MP are believed to be mediated via the intracellular transformation of 6-MP to its active metabolites such as 6-TG and 6-MMP nucleotides. Furthermore, 6-MP metabolites such as 6-TG and 6-MMP were found to correlate with therapeutic efficacy and toxicity associated with 6-MP drug treatment of IBD patients.

The term "anti-inflammatory agent" includes any substance capable of preventing or reducing inflammation. Suitable anti-inflammatory agents include, without limitation, corticosteroids such as prednisolone, methylprednisolone aceponate, mometasone furoate, hydrocortisone, clobetasol propionate, betamethasone, betamethasone valerate, betamethasone dipropionate, dexamethasone, dexamethasone acetate, fluticasone propionate, clobetasone butyrate, beclomethasone dipropionate, and loteprednol etabonate; non-steroidal anti-inflammatory agents such as diclofenac, diflunisal, etodolac, fenbufen, fenoprofen, flurbiprofen, ibuprofen, indomethacin, ketoprofen, ketorolac, meclofenamate, mefenamic acid, meloxicam, nabumetone, naproxen, nimesulide, oxaprozin, piroxicam, salsalate, sulindac, tolmetin, celecoxib, rofecoxib, and 4-biphenylylacetic acid; antibodies such as infliximab; 5-aminosalicylates such as mesalamine, sulphasalazine, balsalazide, and olsalazine; antibiotics such as clindamycin, erythromycin, tetracycline, minocycline, doxycycline, penicillin, ampicillin, carbenicillin, methicillin, cephalosporins, vancomycin, bacitracin, streptomycin, gentamycin, chloramphenicol, fusidic acid, ciprofloxin and other quinolones, sulfonamides, trimethoprim, dapsone, isoniazid, teicoplanin, avoparcin, synercid, virginiamycin, cefotaxime, ceftriaxone, piperacillin, ticarcillin, cefepime, cefpirome, rifampicin, pyrazinamide, ciprofloxacin, levofloxacin, enrofloxacin, amikacin, netilmycin, imipenem, meropenem, and inezolid; pharmaceutically acceptable salts thereof; derivatives thereof; prodrugs thereof; and combinations thereof.

The term "immunosuppressive agent" includes any substance capable of producing an immunosuppressive effect, e.g., the prevention or diminution of the immune response, as by irradiation or by administration of drugs such as anti-metabolites, anti-lymphocyte sera, antibodies, etc. Suitable immunosuppressive agents include, without limitation, azathioprine and metabolites thereof such as those described above; anti-metabolites such as methotrexate; immunosuppressive antibodies such as anti-lymphocyte globulin antibodies, anti-thymocyte globulin antibodies, anti-CD3 antibodies, anti-CD4 antibodies, and antibody-toxin conjugates; mizoribine monophosphate; cyclosporine; scoparone; FK-506 (tacrolimus); FK-778; rapamycin (sirolimus); glatiramer acetate; mycopehnolate; pharmaceutically acceptable salts thereof; derivatives thereof; prodrugs thereof; and combinations thereof.

The term "gene" includes the segment of DNA involved in producing a polypeptide chain; it includes regions preceding and following the coding region, such as the promoter and 3'-untranslated region, respectively, as well as intervening sequences (introns) between individual coding segments (exons).

The term "nucleic acid" or "polynucleotide" includes deoxyribonucleotides or ribonucleotides and polymers thereof in either single- or double-stranded form including, for example, genomic DNA, cDNA and mRNA. This term encompasses nucleic acid molecules of both natural and synthetic origin as well as molecules of linear, circular, or branched configuration representing either the sense or antisense strand, or both, of a native nucleic acid molecule. It is understood that such nucleic acids can be unpurified, purified, or attached, for example, to a synthetic material such as a bead or column matrix. The term also encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), polymorphisms, alleles, orthologs, SNPs, and complementary sequences as well as the sequence explicitly indicated. The term nucleic acid is used interchangeably with gene, cDNA, and mRNA encoded by a gene.

The term "polymorphism" includes the occurrence of two or more genetically determined alternative sequences or alleles in a population. A "polymorphic site" includes the locus at which divergence occurs. Preferred polymorphic sites have at least two alleles, each occurring at a particular frequency in a population. A polymorphic locus may be as small as one base pair (single nucleotide polymorphism, or SNP). Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allele is arbitrarily designated as the reference allele, and other alleles are designated as alternative alleles, "variant alleles," or "variances." The alleles occurring most frequently in a selected population is sometimes referred to as the "wild-type" allele. Diploid organisms may be homozygous or heterozygous for the variant alleles. The variant allele may or may not produce an observable physical or biochemical characteristic ("phenotype") in an individual carrying the variant allele. For example, a variant allele may alter the enzymatic activity of a protein encoded by a gene of interest.

A "single nucleotide polymorphism" or "SNP" occurs at a polymorphic site occupied by a single nucleotide, which is the site of variation between allelic sequences. The site is usually preceded by and followed by highly conserved sequences of the allele (e.g., sequences that vary in less than $\frac{1}{100}$ or $\frac{1}{1000}$ members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

The term "genotype" includes the genetic composition of an organism, including, for example, whether a diploid organism is heterozygous or homozygous for one or more variant alleles of interest.

The term "sample" includes any biological specimen obtained from a subject that contains nucleic acid. Suitable samples for use in the present invention include, without limitation, whole blood, plasma, serum, red blood cells, saliva, urine, stool (i.e., feces), tears, any other bodily fluid, tissue samples (e.g., biopsy), and cellular extracts thereof (e.g., red blood cellular extract).

The term "tolerance" includes the capacity of the body to endure a drug without an adverse drug reaction. In certain instances, the terms "adverse drug reaction" and "side-effect" include an undesirable secondary effect of a drug or therapy. Typical adverse drug reactions include, without limitation, bone marrow suppression, flu-like symptoms, rash, pancreatitis, nausea and vomiting, hepatotoxicity, neutropenia, and combinations thereof. In certain instances, "tolerance" means non-responsive to the therapy.

As used herein, the term "administering" includes oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a thiopurine drug such as AZA or 6-MP is administered at the same time, just prior to, or just after the administration of a second drug (e.g., anti-inflammatory agent, immunosuppressive agent, etc.).

II. General

Oral azathioprine is rapidly converted to 6-mercaptopurine (6-MP) by a nonenzymatic process. Initial 6-MP transformations occur along competing catabolic (XO, xanthine oxidase; TPMT) and anabolic (HPRT, hypoxanthine phosphoribosyltransferase) enzymatic pathways. Once formed by HPRT, 6-TIMP may be transformed into 6-TGN by the rate-limiting enzyme inosine monophosphate dehydrogenase (IMPDH) or methylated into 6-MMP (see, Dubinsky et al., *Gastroenterology* 118:705-713 (2000)). Other non-TGN mechanisms may also be at work.

Xanthine oxidase/dehydrogenase and aldehyde oxidase provide additional pathways for 6 MP/AZA breakdown. Azathioprine is oxidized to 8-hydroxazathioprine by aldehyde oxidase. Xanthine oxidase (XO) converts 6-MP (and 6-TG following guanase conversion to thioxanthine) to thiouric acid (FIG. 1) in human liver and gut (and to a lesser extent in the kidney). Allopurinol inhibits xanthine oxidase, thus theoretically increasing the conversion efficiency of 6-MP to 6-TGN. Bone marrow toxicity arising from co-administration of allopurinol and 6-MP/AZA is well documented and this apparent increased efficacy has even been used as a basis for improving azathioprine response. Furthermore, raised erythrocyte 6-TGN has been demonstrated in the patients receiving allopurinol. The recommended rule of thumb is to reduce 6-MP/AZA dosage to a third or less of normal for a patient also receiving allopurinol.

III. Embodiments

The present invention provides methods for predicting a patient's risk of an adverse drug reaction or tolerance to a 6-mercaptopurine drug (e.g., AZA, 6-MP, or metabolites thereof) by genotyping a patient at a polymorphic site in at least one gene selected from the group consisting of a xanthine dehydrogenase (XDH) gene, molybdenum cofactor sulfurase (MOCOS) gene, aldehyde oxidase (AOX) gene, and a combination thereof. The present invention further provides methods for optimizing therapeutic efficacy in a patient receiving a 6-mercaptopurine drug by determining whether the patient should be given an alternative drug based on the presence or absence of a polymorphism in the xanthine dehydrogenase (XDH) gene, molybdenum cofactor sulfurase (MOCOS) gene, aldehyde oxidase (AOX), and a combination thereof.

The present methods are useful for diseases or disorders such as an immune-mediated gastrointestinal disorder, an autoimmune disease, and graft versus host disease. The methods are especially useful for an immune-mediated gastrointestinal disorder such as inflammatory bowel disease (IBD), e.g., Crohn's disease or ulcerative colitis.

In certain aspects, the methods of the present invention include at least two of the foregoing genes being genotyped. In certain other aspects, at least three of the genes are genotyped in a panel of genes. In certain other aspects, the method further includes genotyping TPMT.

In certain embodiments, the absence of the variant allele is indicative of decreased tolerance to the drug. Suitable 6-mercaptopurine drugs include, for example, 6-mercaptopurine, azathioprine, 6-thioguanine, and 6-methyl-mercaptopurine riboside. Preferably, the administered drug is 6-mercaptopurine or azathioprine.

In certain aspects, the method further includes minimizing a toxicity associated with the drug such as hepatic toxicity, hematological toxicity, and gastrointestinal toxicity.

A. Xanthine Dehydrogenase (XDH)

Xanthine oxidoreductase, which is a molybdenum hydroxylase, exists in two interconvertible forms, xanthine oxidase (EC 1.17.3.2) and xanthine dehydrogenase (EC 1.17.1.4). The conventional accepted role of xanthine oxidoreductase is purine catabolism, wherein it catalyzes the oxidation of hypoxanthine to xanthine and then to uric acid. Although the enzyme exists in two interconvertible forms, the same gene encodes the two enzymes. As used herein, the xanthine dehydrogenase (XDH) gene encodes both xanthine oxidase and xanthine dehydrogenase.

The human xanthine dehydrogenase (XDH) mRNA sequence is available under Genbank Accession No. NM_000379 (SEQ ID NO:1), and the human XDH coding sequence (CDS) is set forth in SEQ ID NO:2. The human XDH genomic sequence is available under Genbank Accession Nos. NC_000002 [REGION: complement (31410692.31491115)] and NT_022184 [REGION: complement (10373121.10453544)].

With respect to the xanthine dehydrogenase (XDH) gene, a polymorphic site such as a variant allele selected from the group consisting of 2211C>T (exon 21) (SEQ ID NO:3), 3030T>C (exon 27) (SEQ ID NO:4), 837C>T (exon 10) (SEQ ID NO:5), 3717G>A (exon 34) (SEQ ID NO:6), 2107A>G (exon 20) (SEQ ID NO:7), 1936A>G (exon 18) (SEQ ID NO:8), and a combination thereof is useful in the present methods. The number (e.g., "2211") in front of each nucleotide substitution (e.g., "C>T") corresponds to the position of that particular nucleotide substitution in the human XDH coding sequence (SEQ ID NO:2). The exon designation (e.g., "exon 21") refers to the specific exon of the human XDH genomic sequence in which the nucleotide substitution is located. For example, "837C>T (exon 10)" corresponds to a C to T nucleotide substitution at position 837 of SEQ ID NO:2; this polymorphism is located in exon 10 of the human XDH genomic sequence. The 837C>T (exon 10) variant allele is especially useful in the present methods.

As described in Example 1, the presence of the 837C>T (exon 10) variant allele protects against side-effects of drugs that produce 6-mercaptopurine. In individuals having this polymorphism, normal drug doses are administered without adverse side-effects.

B. Molybdenum Cofactor Sulfurase (MOCOS)

Polymorphisms in the human molybdenum cofactor sulfurase (MOCOS) gene are also useful in the present methods. The human MOCOS mRNA sequence is available under Genbank Accession No. NM_017947 (SEQ ID NO:9), and the human MOCOS coding sequence (CDS) is set forth in SEQ ID NO:10. The human MOCOS genomic sequence is available under Genbank Accession Nos. NC_000018 [REGION: 32021478.32102683] and NT_010966 [REGION: 15256582.15337787].

In certain instances, the polymorphic site is a variant allele in the molybdenum cofactor sulfurase (MOCOS) gene selected from the group consisting of 2107C>A (exon 11) (SEQ ID NO:11), 509C>T (exon 4) (SEQ ID NO:12), 1072G>A (exon 6) (SEQ ID NO:13), 2600T>C (exon 15) (SEQ ID NO:14), 359G>A (exon 4) (SEQ ID NO:15), and a combination thereof. The number (e.g., "2107") in front of each nucleotide substitution (e.g., "C>A") corresponds to the position of that particular nucleotide substitution in the human MOCOS coding sequence (SEQ ID NO:10). The exon designation (e.g., "exon 11") refers to the specific exon of the human MOCOS genomic sequence in which the nucleotide substitution is located. For example, "2107C>A (exon 11)" corresponds to an A to C nucleotide substitution at position 2107 of SEQ ID NO:10; this polymorphism is located in exon 11 of the human MOCOS genomic sequence. The 2107C>A (exon 11) variant allele is especially useful in the present methods.

In certain individuals, 509C>T, 1072G>A, and 359G>A are very strongly linked and almost always occur together. Two of these SNPs are situated close together in exon 4 and the third (1072G>A) is in exon 6.

As described in Example 1, the presence of the 2107C>A (exon 11) variant allele protects against side-effects of drugs that produce 6-mercaptopurine. In individuals having this polymorphism, normal drug doses are administered without adverse side-effects.

C. Aldehyde Oxidase (AOX) Gene

Aldehyde oxidase (EC 1.2.3.1) is another molybdenum hydroxylase. This cytosolic flavoenzyme generally catalyzes nucleophilic oxidation of N-heterocycles. The complex flavoprotein comprises two identical subunits of molecular weight of 145,000. Each subunit contains one molybdenum, one FAD, and two nonidentical, iron sulfur redox centers as an electron reservoir.

The human aldehyde oxidase (AOX) coding sequence is available under Genbank Accession No. NM_001159 (SEQ ID NO:16), and the human AOX coding sequence (CDS) is set forth in SEQ ID NO:17. The human AOX genomic sequence is available under Genbank Accession Nos. NC_000002 [REGION: 201158976.201244463] and NT_005403 [REGION: 51660148.51745635].

With respect to the AOX gene, a polymorphic site such as a 3404A>G (exon 30) (SEQ ID NO:18) variant allele is useful in the present methods. The number (e.g., "3404") in front of the nucleotide substitution (e.g., "A>G") corresponds to the position of that particular nucleotide substitution in the human AOX coding sequence (SEQ ID NO:17). The exon designation (e.g., "exon 30") refers to the specific exon of the human AOX genomic sequence in which the nucleotide substitution is located. For example, "3404A>G (exon 30)" corresponds to an A to G nucleotide substitution at position 3404 of SEQ ID NO:17; this polymorphism is located in exon 30 of the human AOX genomic sequence.

As described in Example 1, the presence of the 3404A>G (exon 30) variant allele indicates that the individual should be given an alternative drug as a non-responder. In certain aspects, the present invention provides a method for predicting response to a drug providing 6-mercaptopurine in an individual in need thereof, comprising genotyping the aldehyde oxidase gene for the presence of the 3404 A>G (exon 30) variant allele, wherein the presence of the variant allele indicates that the individual should be given an alternative drug.

In certain other optional embodiments, TPMT genotyping is also conducted. TPMT genotyping is useful for predicting the effectiveness of 6-MP therapy in an IBD patient. Heterozygote patients are expected to have lower TPMT activity and should therefore be monitored for high levels of 6-TG for possible toxic levels associated with leukopenia or bone marrow suppression. Homozygous patients deficient in TPMT activity can be treated with lower doses of a 6-MP drug provided that patients are closely monitored for toxicity such as leukopenia. Therefore, TPMT genotyping can be used to predict patient responsiveness to and potential toxicities associated with 6-MP drug therapy. Furthermore, TPMT genotyping can be combined with other methods of the invention to both determine TPMT genotype and to monitor 6-MP metabolites. TPMT genotyping can be particularly valuable when determining a starting dose of 6-MP drug therapy, but can also be useful when adjusting 6-MP drug doses after therapy has begun.

IV. Methods of Genotyping

A variety of means can be used to genotype a subject at a polymorphic site in at least one gene selected from the group consisting of a xanthine dehydrogenase (XDH) gene, molybdenum cofactor sulfurase (MOCOS) gene, and aldehyde oxidase (AOX) gene in the methods of the present invention in order to determine whether a sample (e.g., a nucleic acid sample) contains at least one variant allele. For example, enzymatic amplification of nucleic acid from a subject can be conveniently used to obtain nucleic acid for subsequent analysis. The presence or absence of a variant allele in at least one gene selected from the group consisting of a xanthine dehydrogenase (XDH) gene, molybdenum cofactor sulfurase (MOCOS) gene, and aldehyde oxidase (AOX) gene can also be determined directly from the subject's nucleic acid without enzymatic amplification.

Genotyping of nucleic acid from a subject, whether amplified or not, can be performed using any of various techniques. Useful techniques include, without limitation, polymerase chain reaction (PCR) based analysis, sequence analysis, and electrophoretic analysis, which can be used alone or in combination. As used herein, the term "nucleic acid" means a polynucleotide such as a single- or double-stranded DNA or RNA molecule including, for example, genomic DNA, cDNA and mRNA. This term encompasses nucleic acid molecules of both natural and synthetic origin as well as molecules of linear, circular, or branched configuration representing either the sense or antisense strand, or both, of a native nucleic acid molecule. It is understood that such nucleic acids can be unpurified, purified, or attached, for example, to a synthetic material such as a bead or column matrix.

Material containing nucleic acid is routinely obtained from subjects. Such material is any biological matter from which nucleic acid can be prepared. As non-limiting examples, material can be whole blood, plasma, saliva, cheek swab, or other bodily fluid or tissue that contains nucleic acid. In one embodiment, a method of the present invention is practiced with whole blood, which can be obtained readily by non-invasive means and used to prepare genomic DNA. In another embodiment, genotyping involves amplification of a subject's nucleic acid using the polymerase chain reaction (PCR). Use of PCR for the amplification of nucleic acids is well known in the art (see, e.g., Mullis et al. (Eds.), The Polymerase Chain Reaction, Birkhäuser, Boston, (1994)). In yet another embodiment, PCR amplification is performed using one or more fluorescently labeled primers. In a further embodiment, PCR amplification is performed using one or more labeled or unlabeled primers that contain a DNA minor grove binder.

Any of a variety of different primers can be used to amplify a subject's nucleic acid by PCR. As understood by one skilled in the art, additional primers for PCR analysis can be designed based on the sequence flanking the polymorphic site(s) of interest. As a non-limiting example, a sequence primer can contain from about 15 to about 30 nucleotides of a sequence upstream or downstream of the polymorphic site of interest. Such primers generally are designed to have sufficient guanine and cytosine content to attain a high melting temperature which allows for a stable annealing step in the amplification reaction. Several computer programs, such as Primer Select, are available to aid in the design of PCR primers.

A Taqman® allelic discrimination assay available from Applied Biosystems can be useful for genotyping an individual at a polymorphic site and thereby determining the presence or absence of a variant allele. In a Taqman® allelic discrimination assay, a specific fluorescent dye-labeled probe for each allele is constructed. The probes contain different fluorescent reporter dyes such as FAM and VIC to differentiate amplification of each allele. In addition, each probe has a quencher dye at one end which quenches fluorescence by fluorescence resonance energy transfer. During PCR, each probe anneals specifically to complementary sequences in the nucleic acid from the subject. The 5' nuclease activity of Taq polymerase is used to cleave only probe that hybridizes to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Those skilled in the art understand that improved specificity in allelic discrimination assays can be achieved by conjugating a DNA minor grove binder (MGB) group to a DNA probe as described, e.g., in Kutyavin et al., Nuc. Acids Research 28:655-661 (2000). Minor grove binders include, but are not limited to, compounds such as dihydrocyclopyrroloindole tripeptide (DPI3).

Sequence analysis can also be useful for genotyping a subject at a polymorphic site. A variant allele can be detected by sequence analysis using the appropriate primers, which are designed based on the sequence flanking the polymorphic site of interest, as is known by those skilled in the art. As a non-limiting example, a sequence primer can contain from about 15 to about 30 nucleotides of a sequence that corresponds to a sequence about 40 to about 400 base pairs upstream or downstream of the polymorphic site of interest. Such primers are generally designed to have sufficient guanine and cytosine content to attain a high melting temperature which allows for a stable annealing step in the sequencing reaction.

The term "sequence analysis" means any manual or automated process by which the order of nucleotides in a nucleic acid is determined. As an example, sequence analysis can be used to determine the nucleotide sequence of a sample of DNA. The term sequence analysis encompasses, without limitation, chemical and enzymatic methods such as dideoxy enzymatic methods including, for example, Maxam-Gilbert and Sanger sequencing as well as variations thereof. The term sequence analysis further encompasses, but is not limited to, capillary array DNA sequencing, which relies on capillary electrophoresis and laser-induced fluorescence detection and can be performed using instruments such as the MegaBACE 1000 or ABI 3700. As additional non-limiting examples, the term sequence analysis encompasses thermal cycle sequencing (see, Sears et al., *Biotechniques* 13:626-633 (1992)); solid-phase sequencing (see, Zimmerman et al., *Methods Mol. Cell. Biol.* 3:39-42 (1992); and sequencing with mass spectrometry, such as matrix-assisted laser desorption/ionization time-of-flight mass spectrometry (see, MALDI-TOF MS; Fu et al., *Nature Biotech.* 16:381-384 (1998)). The term sequence analysis further includes, but is not limited to, sequencing by hybridization (SBH), which relies on an array of all possible short oligonucleotides to identify a segment of sequence (see, Chee et al., *Science* 274:610-614 (1996); Drmanac et al., *Science* 260:1649-1652 (1993); and Drmanac et al., *Nature Biotech.* 16:54-58 (1998)). One skilled in the art understands that these and additional variations are encompassed by the term sequence analysis as defined herein.

Electrophoretic analysis also can be useful in genotyping a subject according to the methods of the present invention. "Electrophoretic analysis" as used herein in reference to one or more nucleic acids such as amplified fragments means a process whereby charged molecules are moved through a stationary medium under the influence of an electric field. Electrophoretic migration separates nucleic acids primarily on the basis of their charge, which is in proportion to their size, with smaller molecules migrating more quickly. The term electrophoretic analysis includes, without limitation, analysis using slab gel electrophoresis, such as agarose or polyacrylamide gel electrophoresis, or capillary electrophoresis. Capillary electrophoretic analysis generally occurs inside a small-diameter (50-100 m) quartz capillary in the presence of high (kilovolt-level) separating voltages with separation times of a few minutes. Using capillary electrophoretic analysis, nucleic acids are conveniently detected by UV absorption or fluorescent labeling, and single-base resolution can be obtained on fragments up to several hundred base pairs. Such methods of electrophoretic analysis, and variations thereof, are well known in the art, as described, for example, in Ausubel et al., *Current Protocols in Molecular Biology* Chapter 2 (Supplement 45) John Wiley & Sons, Inc. New York (1999).

Restriction fragment length polymorphism (RFLP) analysis can also be useful for genotyping a subject at a polymorphic site in the ITPA gene according to the methods of the present invention (see, Jarcho et al. in Dracopoli et al., *Current Protocols in Human Genetics* pages 2.7.1-2.7.5, John Wiley & Sons, New York; Innis et al., (Ed.), *PCR Protocols*, San Diego: Academic Press, Inc. (1990)). As used herein, "restriction fragment length polymorphism analysis" includes any method for distinguishing polymorphic alleles using a restriction enzyme, which is an endonuclease that catalyzes degradation of nucleic acid following recognition of a specific base sequence, generally a palindrome or inverted repeat. One skilled in the art understands that the use of RFLP analysis depends upon an enzyme that can differentiate a variant allele from a wild-type or other allele at a polymorphic site.

In addition, allele-specific oligonucleotide hybridization can be useful for genotyping a subject in the methods of the present invention. Allele-specific oligonucleotide hybridization is based on the use of a labeled oligonucleotide probe having a sequence perfectly complementary, for example, to the sequence encompassing the variant allele. Under appropriate conditions, the variant allele-specific probe hybridizes to a nucleic acid containing the variant allele but does not hybridize to the one or more other alleles, which have one or more nucleotide mismatches as compared to the probe. If desired, a second allele-specific oligonucleotide probe that matches an alternate (e.g., wild-type) allele can also be used. Similarly, the technique of allele-specific oligonucleotide amplification can be used to selectively amplify, for example, a variant allele by using an allele-specific oligonucleotide primer that is perfectly complementary to the nucleotide sequence of the variant allele but which has one or more mismatches as compared to other alleles (Mullis et al., supra). One skilled in the art understands that the one or more nucleotide mismatches that distinguish between the variant allele and other alleles are often located in the center of an allele-specific oligonucleotide primer to be used in the allele-specific oligonucleotide hybridization. In contrast, an allele-specific oligonucleotide primer to be used in PCR amplification generally contains the one or more nucleotide mismatches that distinguish between the variant and other alleles at the 3' end of the primer.

A heteroduplex mobility assay (HMA) is another well-known assay that can be used for genotyping at a polymorphic site in the methods of the present invention. HMA is useful for detecting the presence of a variant allele since a DNA duplex carrying a mismatch has reduced mobility in a polyacrylamide gel compared to the mobility of a perfectly base-paired duplex (see, Delwart et al., *Science,* 262:1257-1261 (1993); White et al., *Genomics,* 12:301-306 (1992)).

The technique of single strand conformational polymorphism (SSCP) can also be useful for genotyping at a polymorphic site in the methods of the present invention (see, Hayashi, *Methods Applic.,* 1:34-38 (1991)). This technique is used to detect variant alleles based on differences in the secondary structure of single-stranded DNA that produce an altered electrophoretic mobility upon non-denaturing gel electrophoresis. Variant alleles are detected by comparison of the electrophoretic pattern of the test fragment to corresponding standard fragments containing known alleles.

Denaturing gradient gel electrophoresis (DGGE) can be useful in the methods of the present invention. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (see, Sheffield et al., "Identifying DNA Polymorphisms by Denaturing Gradient Gel Electrophoresis" in Innis et al., supra, 1990).

Other molecular methods useful for genotyping a subject at a polymorphic site are known in the art and useful in the methods of the present invention. Such well-known genotyping approaches include, without limitation, automated sequencing and RNAase mismatch techniques (see, Winter et al., *Proc. Natl. Acad. Sci.,* 82:7575-7579 (1985)). Furthermore, one skilled in the art understands that, where the presence or absence of multiple variant alleles is to be determined, individual variant alleles can be detected by any combination of molecular methods. See, in general, Birren et al. (Eds.) *Genome Analysis: A Laboratory Manual Volume* 1 (Analyzing DNA) New York, Cold Spring Harbor Laboratory Press (1997). In addition, one skilled in the art understands that multiple variant alleles can be detected in individual reactions or in a single reaction (a "multiplex" assay).

In view of the above, one skilled in the art realizes that the methods of the present invention for predicting tolerance or optimizing therapeutic efficacy to a thiopurine drug by genotyping a subject in at least one gene selected from the group consisting of xanthine dehydrogenase (XDH) gene, molybdenum cofactor sulfurase (MOCOS) gene, and aldehyde oxidase (AOX) gene can be practiced using one or any combination of the well-known assays described above or other assays known in the art.

V. Diseases

The methods of the invention relate to treatment of an immune-mediated gastrointestinal disorder. As used herein, the term "immune-mediated gastrointestinal disorder" or "immune-mediated GI disorder" includes a non-infectious disease of the gastrointestinal tract or bowel that is mediated by the immune system or cells of the immune system. Immune-mediated gastrointestinal disorders include, for example, inflammatory bowel diseases (IBD) such as Crohn's disease and ulcerative colitis, lymphocytic colitis, microscopic colitis, collagenous colitis, autoimmune enteropathy, allergic gastrointestinal disease and eosinophilic gastrointestinal disease.

The methods of the invention are particularly useful for treating IBD, or subtypes thereof, which has been classified into the broad categories of Crohn's disease and ulcerative colitis. As used herein, "a subject having inflammatory bowel disease" is synonymous with the term "a subject diagnosed with having an inflammatory bowel disease," and means a patient having Crohn's disease or ulcerative colitis. Crohn's disease (regional enteritis) is a disease of chronic inflammation that can involve any part of the gastrointestinal tract. Commonly, the distal portion of the small intestine (ileum) and cecum are affected. In other cases, the disease is confined to the small intestine, colon or anorectal region. Crohn's disease occasionally involves the duodenum and stomach, and more rarely the esophagus and oral cavity.

Ulcerative colitis (UC) is a disease of the large intestine characterized by chronic diarrhea with cramping abdominal pain, rectal bleeding, and loose discharges of blood, pus and mucus. The manifestations of ulcerative colitis vary widely. A pattern of exacerbations and remissions typifies the clinical course of most UC patients (70%), although continuous symptoms without remission are present in some patients with UC. Local and systemic complications of UC include arthritis, eye inflammation such as uveitis, skin ulcers and liver disease. In addition, ulcerative colitis and especially long-standing, extensive disease is associated with an increased risk of colon carcinoma.

In comparison with Crohn's disease, which is a patchy disease with frequent sparing of the rectum, ulcerative colitis is characterized by a continuous inflammation of the colon that usually is more severe distally than proximally. The inflammation in ulcerative colitis is superficial in that it is usually limited to the mucosal layer and is characterized by an acute inflammatory infiltrate with neutrophils and crypt abscesses. In contrast, Crohn's disease affects the entire thickness of the bowel wall with granulomas often, although not always, present. Disease that terminates at the ileocecal valve, or in the colon distal to it, is indicative of ulcerative colitis, while involvement of the terminal ileum, a cobblestone-like appearance, discrete ulcers or fistulas suggest Crohn's disease. 5'-monophosphate. Measuring 6-MMP can include 6-methylmercaptopurine and 6-methylthioinosine 5'-monophosphate, and can also include 6-methylthioinosine di- and tri-phosphate, as well as 6-methyl thioguanosine.

VI. Examples

The following examples are intended to illustrate but not limit the present invention.

Example 1

This example illustrates the use of the various SNPs of the present invention.

A. Patients

Patients were recruited at the point of starting azathioprine therapy. One hundred and sixty-eight (168) patients from this cohort were included in the study, selected on the availability of complete clinical data and adequate DNA. Complete remission was defined by symptom scores and absence of steroid use. Treatment failure was defined by recourse to surgery, alternative immunomodulator or biologic therapy. Side-effects were included in the analysis only if they were the cause of treatment withdrawal.

B. Laboratory Methods

1. DNA Extraction

DNA was extracted from whole blood collected in EDTA bottle using the QIAmp DNA Mini Kit 250 (Qiagen Ltd. Crawley, UK). Briefly, 200%l of whole blood was lysed by addition of protease enzyme and buffer AL from the Qiagen kit. This mixture was vortexed and then incubated at 56° C. for 10 minutes to digest and denature blood proteins. 200 μl of 100% ethanol was then added, the mixture was vortexed and transferred to a QIAmp spin column within a 2 ml collection tube. These tubes were then centrifuged at 800 rpm for 1 minute to adsorb the DNA onto the silica-gel membrane of the spin column. The column then underwent washing steps to remove contaminants that could interfere with the PCR reaction. The column was then transferred to a clean collection tube and the DNA eluted from the column membrane by addition of 200 μl of QIAgen buffer AE and a final centrifuge step of 8000 rpm for 1 minute. On average, this method produced 6 μg of total DNA in 20-30 kb lengths from 200 μl of whole blood. This DNA was mixed with 50 μl of tris-EDTA (×1 mixture) to inhibit DNAases and stored in a freezer at −20° C.

2. Real-Time PCR

SNPs were selected for analysis in the three target genes: xanthine dehydrogenase (XDH), molybdenum cofactor sulfurase, (MOCOS) and aldehyde oxidase (AOX). Only coding SNPs were selected and the choice was further narrowed according to reported gene frequencies in the Caucasian population and, where possible, by choosing SNPs that encoded a non-conservative change in an amino acid residue. Probes for the SNPs selected were obtained from Applied Biosystems (Warrington, UK). Details are shown in Table 1.

Patients were genotyped by real-time PCR using a Biorad Miniopticon (Bio-Rad, Hemel Hempstead, UK). 1.8 μl of DNA was mixed with Absolute QPCR Mix (Abgene, Epsom, UK) and SNP mix (Applied Biosystems, Warrington, UK) and diluted up to volume with DNA-free water, according to the manufacturers' instructions. PCR conditions were 15 minutes enzyme activation at 95° C., then 42 cycles of: denaturation (15 secs at 95° C.) and anneal/extension (1 min at 60° C.).

TABLE 1

SNP information.

| dbSNP rs number | Gene | Exon | cDNA base change | Amino acid substitution | Frequency |
|---|---|---|---|---|---|
| rs2295475 | XDH 2p23.1a | 21 | 2211C > T | Ile737Ile | 0.31 |
| rs1884725 | XDH 2p23.1a | 27 | 3030T > C | Phe1010Phe | 0.23 |
| rs4407290 | XDH 2p23.1a | 10 | 837C > T | Val279Val | 0.02 |
| rs207440 | XDH 2p23.1a | 34 | 3717G > A | Glu1239Glu | 0.06 |
| rs17011368 | XDH 2p23.1a | 20 | 2107A > G | Ile703Val | 0.05 |
| rs17323225 | XDH 2p23.1a | 18 | 1936A > G | Ile646Val | 0.05 |
| rs594445 | MOCOS 18q12.2a | 11 | 2107C > A | His703Asn | 0.34 |
| rs623053 | MOCOS 18q12.2a | 4 | 509C > T | Thr170Ile | 0.03 |
| rs678560 | MOCOS 18q12.2a | 6 | 1072G > A | Val358Met | 0.03 |
| rs1057251 | MOCOS 18q12.2a | 15 | 2600T > C | Val867Ala | 0.10 |
| rs3744900 | MOCOS 18q12.2a | 4 | 359G > A | Ser120Asn | 0.03 |
| n/a | AOX 2q33.1e | 30 | 3404A > G | Asn1135Ser | 0.16 |

C—cytosine, T—thymine, G—guanine, A—adenine. Ile—isoleucine, Phe—phenylalanine, Val—valine, Glu—glutamate, Asn—asparagine, His—histidine, Thr—threonine, Met—methionine, Ala—alanine. Frequencies are those quoted for the Caucasian population.

3. Statistics

Associations between side-effects and genotype were determined using contingency tables and Chi-squared and Fisher exact tests were applied. Effect sizes were measured using odds ratios and confidence intervals.

C. Results

The gene frequencies identified were similar to those reported in SNP databases. The details of these frequencies are displayed in Table 2.

TABLE 2

Gene frequencies in the present cohort compared with reported frequencies in SNP databases (http://www.ncbi.nlm.nih.gov/SNP).

| SNP | Expected frequency | Documented frequency |
|---|---|---|
| XDH 2211C > T | 0.31 | 0.25 |
| XDH 3030T > C | 0.23 | 0.23 |
| XDH 837C > T | 0.02 | 0.04 |
| XDH 3717G > A | 0.06 | 0.06 |
| XDH 2107A > G | 0.05 | 0.08 |
| XDH 1936A > G | 0.05 | 0.08 |
| MOCOS 2107C > A | 0.34 | 0.29 |
| MOCOS 509C > T | 0.03 | 0.06 |
| MOCOS 1072G > A | 0.03 | 0.06 |
| MOCOS 2600T > C | 0.10 | 0.10 |
| MOCOS 359G > A | 0.03 | 0.05 |
| AOX 3404A > G | 0.16 | 0.12 |

SNPs MOCOS 509C>T, 1072G>A, and 359G>A were very strongly linked and almost always occurred together. Two of these SNPs were situated close together in exon 4 and the third (MOCOS 1072G>A) was at quite a distance in exon 6. In analysis of functional relevance, these SNPs have therefore been analyzed together.

SNPs were analyzed for association with side-effects or non-response. The SNP XDH 837C>T was found to protect against side-effects to azathioprine (p=0.046). A trend towards protection from side-effects was seen in a few other SNPs in both XDH and MOCOS. Removing those side-effects which are already accounted for by a TPMT polymorphism from the analysis strengthened the association between SNP MOCOS 2107C>A and protection against side-effects. The strongest association detected was between the presence of SNP AOX 3404A>G and a lack of response to azathioprine (p=0.006).

In total, there were 35 patients deemed to have no response to azathioprine and 7 who were partial responders. TGN levels were available for 34 of these patients. These levels would suggest that 11 of this group were poorly concordant with their treatment, with average TGN levels less than 50 μmol/8×10$^8$ RBC over the course of the study. Among the remaining patients there was no significant difference seen between the TGN levels in those who were wild-type and those who are heterozygous for the AOX SNP.

TABLE 3

The association between each SNP and outcome.

| SNP | p-value for response to treatment | p-value for side-effects on treatment |
|---|---|---|
| XDH 2211C > T | 0.891 | 0.174 |
| XDH 3030T > C | 0.724 | 0.921 |
| XDH 837C > T | 0.933 | 0.046 |
| XDH 3717G > A | 0.739 | 0.133 |
| XDH 2107A > G | 0.391 | 0.631 |
| XDH 1936A > G | 1.0 | 0.792 |
| MOCOS 2107C > A | 0.531 | 0.151 |
| MOCOS 509C > T, 1072G > A & 359G > A | 0.634 | 0.146 |
| MOCOS 2600T > C | 0.217 | 0.139 |
| AOX 3404A > G | 0.006 | 0.552 |

Responders are those defined as having a complete response (therapeutic target reached with no steroid therapy) and side-effects must have caused therapy to be discontinued. Statistics have been performed using the chi-squared test using dominant model to look for clinically relevant associations. The figures given in the data cells are patient numbers presented as wild-type; heterozygous; homozygous.

D. Discussion

The association between SNPs in XDH and MOCOS and a protective effect against side-effects is interesting. No other protective SNP has ever been demonstrated in this context. This association would support the theory generated by in vitro experiments that metabolites produced by XDH can be toxic, and would suggest that the reactive oxygen species produced by XDH are responsible for a proportion of side-effects experienced on thiopurine treatment.

This provides proof of the concept that TPMT is not the only pharmacogenetically interesting enzyme in thiopurine metabolism.

With respect to the AOX SNP, this is very useful in enabling personalized selection of immunomodulators, which has long been one of the aims of pharmacogenetics in this field.

Example 2

This example illustrates the use of allopurinol and azathioprine as combination therapy.

A. Patient's Phenotype

Patients present with low levels of 6-TGN, i.e., below therapeutic levels, and moderate levels of 6-MMP when taking a normal dose of azathioprine or equivalent. Under these circumstances, the clinician will increase the dose of azathioprine, which results in a minor yet still non-therapeutic increase in 6-TGN levels, but a toxic increase of 6-MMP level. Patients have normal levels of TPMT.

B. Protocol

Patients should be genotyped for related SNPs in their xanthine dehydrogenase (XDH) gene, molybdenum cofactor sulfurase (MOCOS) gene, aldehyde oxidase (AOX) gene or a combination thereof. From these results a genotype may be used as to indicate that allopurinol should be considered as adjunct therapy.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, Genbank Accession Nos., and dbSNP Accession Nos., are incorporated herein by reference for all purposes.

What is claimed is:

1. A method for identifying a human subject who is likely to lack response to azathioprine (AZA) or 6-mercaptopurine (6-MP), said method comprising:
   (a) genotyping nucleic acid in a sample from said subject for the presence of the 3404 A to G mutation in the Aldehyde oxidase (AOX) coding sequence;
   (b) detecting a G at position 3404 in the AOX coding sequence; and
   (c) identifying the subject as likely to lack response to AZA or 6-MP when a G at position 3404 in the AOX coding sequence is detected.

2. The method of claim 1, wherein said individual has a disease or disorder selected from the group consisting of an immune-mediated gastrointestinal disorder, an autoimmune disease, and graft versus host disease.

3. The method of claim 2, wherein said immune-mediated gastrointestinal disorder is inflammatory bowel disease.

4. The method of claim 1, wherein the method further comprises genotyping thiopurine methyltransferase (TPMT).

5. A method for treating a human subject having inflammatory bowel disease (IBD), said method comprising:
   (a) genotyping nucleic acid in a sample from said subject for the presence of the 3404 A to G mutation in the Aldehyde oxidase (AOX) coding sequence;
   (b) detecting a G at position 3404 in the AOX coding sequence; and
   (c) treating the human subject having the presence of a G at position 3404 in the AOX coding sequence with a drug other than AZA or 6-MP.

6. The method of claim 5, wherein said drug other than AZA or 6-MP is an anti-inflammatory agent.

7. The method of claim 6, wherein said anti-inflammatory agent is infliximab.

8. The method of claim 5, wherein said drug other than AZA or 6-MP is an immunosuppressive agent.

9. The method of claim 5, wherein the human subject having IBD has Crohn's disease.

10. The method of claim 1 or 5, wherein the method further comprises genotyping the xanthine dehydrogenase (XDH) gene for a variant allele selected from the group consisting of 2211C>T (exon 21), 3030T>C (exon 27), 837 C>T (exon 10), 37170>A (exon 34), 2107A>G (exon 20), 1936 A>G (exon 18) and a combination thereof.

11. The method of claim 1 or 5, wherein the method further comprises genotyping the molybdenum cofactor sulfurase (MOCOS) gene for a variant allele selected from the group consisting of 2107C>A (exon 11), 509 C>T (exon 4), 1072 G>A (exon 6), 2600T>C (exon 15), 3590>A (exon 4) and a combination thereof.

* * * * *

UNITED STATES PATENT AND TRADEMARK OFFICE
CERTIFICATE OF CORRECTION

| | | |
|---|---|---|
| PATENT NO. | : 7,919,251 B2 | |
| APPLICATION NO. | : 12/248866 | |
| DATED | : April 5, 2011 | |
| INVENTOR(S) | : Sanderson et al. | |

It is certified that error appears in the above-identified patent and that said Letters Patent is hereby corrected as shown below:

In the Claims:

Claim 11, Column 78, Line 64: please delete "3590>A" and insert --359G>A--.

Signed and Sealed this
Fifteenth Day of November, 2011

David J. Kappos
*Director of the United States Patent and Trademark Office*

SEQUENCE LISTING

```
<160> NUMBER OF SEQ ID NOS: 18

<210> SEQ ID NO 1
<211> LENGTH: 5717
<212> TYPE: DNA
<213> ORGANISM: Homo sapiens
<220> FEATURE:
<223> OTHER INFORMATION: molybdenum hydroxylase xanthine dehydrogenase
      (XDH), xanthine oxidoreductase (XOR), xanthine oxidase (XO) cDNA

<400> SEQUENCE: 1
gtcacagagc agtgataact acctgccagt gtctcttagg agtgaggtac ctggagttcg      60
gggaccccaa cctgtgacaa tgacagcaga caaattggtt ttctttgtga atggcagaaa     120
ggtggtggag aaaaatgcag atccagagac aacccttttg gcctacctga aagaaaagtt     180
ggggctgagt ggaaccaagc tcggctgtgg agaggggggc tgcggggctt gcacagtgat     240
gctctccaag tatgatcgtc tgcagaacaa gatcgtccac tttctgcca atgcctgcct      300 ggcccccatc tgctccttgc accatgttgc agtgacaact gtggaaggaa taggaagcac     360
caagacgagg ctgcatcctg tgcaggagag aattgccaaa agccacggct cccagtgcgg     420
gttctgcacc cctggcatcg tcatgagtat gtacacactg ctccggaatc agcccgagcc     480
caccatggag gagattgaga atgccttcca aggaaatctg tgccgctgca caggctacag     540
acccatcctc cagggcttcc ggaccttgc cagggatggt ggatgctgtg gaggagatgg     600
gaataatcca aattgctgca tgaaccagaa gaaagaccac tcagtcagcc tctcgccatc     660
tttattcaaa ccagaggagt tcacgcccct ggatccaacc caggagccca tttttcccc     720 agagttgctg aggctgaaag acactcctcg gaagcagctg cgatttgaag gggagcgtgt     780
gacgtggata caggcctcaa ccctcaagga gctgctggac ctcaaggctc agcaccctga     840
cgccaagctg gtcgtgggga acacggagat tggcattgag atgaagttca agaatatgct     900
gtttcctatg attgtctgcc cagcctggat ccctgagctg aattcggtag aacatggacc     960
cgacggtatc tcctttggag ctgcttgccc cctgagcatt gtggaaaaaa ccctggtgga    1020
tgctgttgct aagcttcctg cccaaaagac agaggtgttc agagggtcc tggagcagct    1080 gcgctggttt gctgggaagc aagtcaagtc tgtggcgtcc gttggaggga acatcatcac    1140
tgccagcccc atctccgacc tcaaccccgt gttcatggcc agtggggcca agctgacact    1200
tgtgtccaga ggcaccagga gaactgtcca gatggaccac accttcttcc ctggctacag    1260
aaagaccctg ctgagcccgg aggagatact gctctccata gagatcccct acagcaggga    1320
gggggagtat ttctcagcat tcaagcaggc ctcccggaga gaagatgaca ttgccaaggt    1380
```

```
aaccagtggc atgagagttt tattcaagcc aggaaccaca gaggtacagg agctggccct    1440
ttgctatggt ggaatggcca acagaaccat ctcagccctc aagaccactc agaggcagct    1500
ttccaagctc tggaaggagg agctgctgca ggacgtgtgt gcaggactgg cagaggagct    1560
gcatctgcct cccgatgccc ctggtggcat ggtggacttc cggtgcaccc tcaccctcag    1620
cttcttcttc aagttctacc tgacagtcct tcagaagctg gccaagagaa acctggaaga    1680
caagtgtggt aaactggacc ccactttcgc cagtgcaact ttactgtttc agaaagaccc    1740
cccagccgat gtccagctct tccaagaggt gcccaagggt cagtctgagg aggacatggt    1800
gggccggccc ctgccccacc tggcagcgga catgcaggcc tctggtgagg ccgtgtactg    1860 tgacgcatt cctcgctacg agaatgagct gtctctccgg ctggtcacca gcacccgggc    1920
ccacgccaag atcaagtcca tagatacatc agaagctaag aaggttccag ggtttgtttg    1980
tttcatttcc gctgatgatg ttcctgggag taacataact ggaatttgta atgatgagac    2040
agtctttgcg aaggataagg ttacttgtgt tgggcatatc attggtgctg tggttgctga    2100
caccccggaa cacacacaga gagctgccca aggggtgaaa atcacctatg aagaactacc    2160
agccattatc acaattgagg atgctataaa gaacaactcc ttttatggac ctgagctgaa    2220
gatcgagaaa ggggacctaa agaaggggtt ttccgaagca gataatgttg tgtcagggga    2280
gatatacatc ggtggccaag agcacttcta cctggagact cactgcacca ttgctgttcc    2340
aaaaggcgag gcaggggaga tggagctctt tgtgtctaca cagaacacca tgaagaccca    2400
gagctttgtt gcaaaaatgt tgggggttcc agcaaaccgg attgtggttc gagtgaagag    2460
aatgggagga ggctttggag gcaaggagac ccggagcact gtggtgtcca cggcagtggc    2520
cctggctgca tataagaccg gccgcccctg tcgcgatgca tg ctggaccgtg atgaggacat    2580
gctgataact ggtggcagac atcccttcct ggccagatac aaggttggct tcatgaagac    2640
tgggacagtt gtggctcttg aggtggacca cttcagcaat gtggggaaca cccaggatct    2700
ctctcagagt attatggaac gagctttatt ccacatggac aactgctata aaatccccaa    2760
catccggggc actgggcggc tgtgcaaaac caaccttccc tccaacacgg ccttccgggg    2820
ctttgggggg ccccagggga tgctcattgc cgagtgctgg atgagtgaag ttgcagtgac    2880
ctgtgggatg cctgcagagg aggtgcggag aaaaaacctg tacaaagaag gggacctgac    2940
acacttcaac cagaagcttg agggtttcac cttgcccaga tgctgggaag aatgcctagc    3000
aagctctcag tatcatgctc ggaagagtga ggttgacaag ttcaacaagg agaattgttg    3060
gaaaaagaga ggattgtgca taattcccac caagtttgga ataagctta cagttccttt    3120 tctgaatcag gcaggagccc tacttcatgt gtacacagat ggctctgtgc tgctgaccca    3180
cggggggact gagatgggcc aaggccttca taccaaaatg gtccaggtgg ccagtagagc    3240
tctgaaaatc cccaccctcta agatttatat cagcagacaa gcactaaca ctgtgcccaa    3300 cacctctccc acggctgcct ctgtcagcgc tgacctcaat ggacaggccg tctatgcggc    3360
ttgtcagacc atcttgaaaa ggctggaacc ctacaagaag aagaatccca gtggctcctg    3420
ggaagactgg gtcacagctg cctacatgga cacagtgagc ttgtctgcca ctgggtttta    3480
tagaacaccc aatctgggct acagctttga gactaactca gggaacccct tccactactt    3540
cagctatggg gtggcttgct ctgaagtaga aatcgactgc ctaacaggag atcataagaa    3600
cctccgcaca gatattgtca tggatgttgg ctccagtcta aaccctgcca ttgatattgg    3660
acaggtggaa ggggcatttg tccagggcct tggcctcttc acccctagagg agctacacta    3720 ttccccccgag gggagcctgc acacccgtgg ccctagcacc tacaagatcc cggcatttgg    3780
```

```
cagcatcccc attgagttca gggtgtccct gctccgcgac tgccccaaca agaaggccat    3840
ctatgcatcg aaggctgttg gagagccgcc cctcttcctg gctgcttcta tcttctttgc    3900
catcaaagat gccatccgtg cagctcgagc tcagcacaca ggtaataacg tgaaggaact    3960
cttccggcta gacagccctg ccaccccgga gaagatccgc aatgcctgcg tggacaagtt    4020
caccaccctg tgtgtcactg tgtcccaga aaactgcaaa ccctggtctg tgagggtcta    4080
aagagagagt cctcagcaga gtcttcttgt gctgcctttg ggcttccatg gagcaggagg    4140
aacataccac agaacatgga tctattaaag tcacagaatg acagacctgt gatttgtcaa    4200
gatgggattt ggaagacaag tgaatgcaat ggaagatttt gatcaaaaat gtaatttgta    4260
aacacaatga taagcaaatt caaaactgtt atgcctaaat ggtgaatatg caattaggat    4320
cattttctgt ctgttttaat catgtatctg gaatagggtc gggaagggtt tgtgctattc    4380
cccacttact ggacagccct tataacctca agttctgatg gtgtctgtcc tttgaagagg    4440
attcccacaa acctctagaa gcttaaaccg aagttacttt aaatcgtgtg ccttcctgtg    4500
aaagcctggc cttcaaacca atgaacagca agcataacc ttgaatctat actcaaattt     4560
tgcaatgagg cagtggggta aggttaaatc ctctaaccat cttgaatca ttggaaagaa     4620 taagaatga aacaaattca aggttaattg gatctgattt tgtgaagctg cataaagcaa     4680
gattactcta taatacaaaa atccaaccaa ctcaattatt gagcacgtac aatgttctag    4740
atttctttcc cttcctcttt gaagagaata tttgtattcc aaatactctt tgagtattta    4800
caaaaaagat tatgtttaat ctttacattt gaagccaaag taatttccac ctagaaatga    4860
tgctatcagt cctggcatgg tggctcaccc ctataatccc agcactttgg gaggctaagg    4920
caggagaatt gcttgagccc agcagtttga accagcctg gcaacatag agagctcctg      4980 tctttaaaaa aaatttttt aattagttgg tcttgatagt gcatgcctgt agtcccaact     5040
acttgaaagg ctgaggtgga gagatcattt gagctcagga ggttgaggct gcagtgagct    5100
atgattgcgc cactgcactc ctgcctgagc gactgagcaa gatcttgtct ctgaagaaaa    5160 aaaagaaat aaaaatgctg ctatcaaaat caagcccaac cagaggtaga agagccaaga     5220
agcctgggtt ctcatcctag ctctgtctct tctgtctcta tctttgtgat cttggactgt    5280
caattcccct tcctgtgatc cattttactg caaacataag ggttgcagta aagggttgtc    5340
tcacgtcttc tgctttaaaa gcctataaat atatgacctg aaaactccag ttacataaag    5400
gatctgcagc tatctaaggc ttggttttct tactgtcata tgatacctgg gtctaatgaa    5460
ctctgctgag atcacctcaa gtttctgcgg ttggtaaaga gaacaaggga agaacaaaca    5520
tcccttttat tgctccaaat ggtgatttaa tccctacatg gtgctgggtg gacaatgtgt    5580
cactgtcaca tgccttcact gtataaatcc aaccttctgc cagagagaat ctgtggttct    5640
ggccatggag ggaggatagt ggaaatgata tagttggact ggtgcttgat gtcactaata    5700
aatgaaactg tcagctg                                                   5717
```

<210> SEQ ID NO 2
<211> LENGTH: 4002
<212> TYPE: DNA
<213> ORGANISM: Homo sapiens
<220> FEATURE:
<223> OTHER INFORMATION: molybdenum hydroxylase xanthine dehydrogenase
     (XDH), xanthine oxidoreductase (XOR), xanthine oxidase (XO)
     coding sequence (CDS)
<221> NAME/KEY: CDS
<222> LOCATION: (1)...(4002)
<223> OTHER INFORMATION: molybdenum hydroxylase xanthine dehydrogenase
     (XDH), xanthine oxidoreductase (XOR), xanthine oxidase (XO)

<400> SEQUENCE: 2

```
atgacagcag acaaattggt tttctttgtg aatggcagaa aggtggtgga gaaaaatgca      60
gatccagaga caacccttttt ggcctacctg agaagaaagt tggggctgag tggaaccaag    120
ctcggctgtg gagaggggg ctgcggggct tgcacagtga tgctctccaa gtatgatcgt     180
ctgcagaaca agatcgtcca cttttctgcc aatgcctgcc tggcccccat ctgctccttg    240
caccatgttg cagtgacaac tgtggaagga ataggaagca ccaagacgag gctgcatcct    300
gtgcaggaga gaattgccaa aagccacggc tcccagtgcg ggttctgcac ccctggcatc    360
gtcatgagta tgtacacact gctccggaat cagcccgagc ccaccatgga ggagattgag    420
aatgccttcc aaggaaatct gtgccgctgc acaggctaca gacccatcct ccagggcttc    480
cggacctttg ccagggatgg tggatgctgt ggaggagatg ggaataatcc aaattgctgc    540
atgaaccaga agaaagacca ctcagtcagc ctctcgccat ctttattcaa accagaggag    600
ttcacgcccc tggatccaac ccaggagccc atttttcccc cagagttgct gaggctgaaa    660
gacactcctc ggaagcagct gcgatttgaa ggggagcgtg tgacgtggat acaggcctca    720
accctcaagg agctgctgga cctcaaggct cagcaccctg acgccaagct ggtcgtgggg    780
aacacggaga ttggcattga gatgaagttc aagaatatgc tgtttcctat gattgtctgc    840
ccagcctgga tccctgagct gaattcggta aacatggac cgacggtat ctcctttgga     900
gctgcttgcc ccctgagcat tgtggaaaaa accctggtgg atgctgttgc taagcttcct    960
gcccaaaaga cagaggtgtt cagagggtc ctggagcagc tgcgctggtt tgctgggaag   1020
caagtcaagt ctgtggcgtc cgttggaggg aacatcatca ctgccagccc catctccgac   1080
ctcaaccccg tgttcatggc cagtggggcc aagctgacac ttgtgtccag aggcaccagg   1140
agaactgtcc agatggacca caccttcttc cctggctaca aaagacccct gctgagcccg   1200
gaggagatac tgctctccat agagatcccc tacagcaggg aggggagta tttctcagca    1260
ttcaagcagg cctcccggag agaagatgac attgccaagg taaccagtgg catgagagtt   1320
ttattcaagc aggaaccac agaggtacag gagctggccc tttgctatgg tggaatggcc    1380
aacagaacca tctcagccct caagaccact cagaggcagc tttccaagct ctggaaggag   1440
gagctgctgc aggacgtgtg tgcaggactg gcagaggagc tgcatctgcc tcccgatgcc   1500
cctggtggca tggtggactt ccggtgcacc ctcaccctca gcttcttctt caagttctac   1560
ctgacagtcc ttcagaagct gggccaagag aacctggaag acaagtgtgg taaactggac   1620
cccactttcg ccagtgcaac tttactgttt cagaaagacc cccagccga tgtccagctc    1680
ttccaagagg tgcccaaggg tcagtctgag gaggacatgg tgggccggcc cctgccccac   1740
ctggcagcgg acatgcaggc ctctggtgag gccgtgtact gtgacgacat tcctcgctac   1800
gagaatgagc tgtctctccg gctggtcacc agcacccggg cccacgccaa gatcaagtcc   1860
atagatacat cagaagctaa gaaggttcca gggtttgttt gtttcatttc cgctgatgat   1920
gttcctggga gtaacataac tggaatttgt aatgatgaga cagtctttgc gaaggataag   1980
gttacttgtg ttgggcatat cattggtgct gtggttgctg acaccccgga acacacacag   2040
agagctgccc aagggtgaa atcacctat gaagaactac cagccattat cacaattgag    2100
gatgctataa agaacaactc cttttatgga cctgagctga gatcgagaa aggggaccta   2160
aagaaggggt tttccgaagc agataatgtt gtgtcagggg agatatacat cggtggccaa   2220
gagcacttct acctggagac tcactgcacc attgctgttc caaaggcga ggcagggag    2280
atggagctct ttgtgtctac acagaacacc atgaagaccc agagctttgt tgcaaaaatg   2340
```

| | |
|---|---|
| ttgggggttc cagcaaaccg gattgtggtt cgagtgaaga gaatgggagg aggctttgga | 2400 |
| ggcaaggaga cccggagcac tgtggtgtcc acggcagtgg ccctggctgc atataagacc | 2460 |
| ggccgccctg tgcgatgcat gctggaccgt gatgaggaca tgctgataac tggtggcaga | 2520 |
| catcccttcc tggccagata caaggttggc ttcatgaaga ctgggacagt tgtggctctt | 2580 |
| gaggtggacc acttcagcaa tgtggggaac acccaggatc tctctcagag tattatggaa | 2640 |
| cgagctttat tccacatgga caactgctat aaaatcccca acatccgggg cactgggcgg | 2700 |
| ctgtgcaaaa ccaaccttcc ctccaacacg gccttccggg ctttggggg ccccagggg | 2760 |
| atgctcattg ccgagtgctg gatgagtgaa gttgcagtga cctgtgggat gcctgcagag | 2820 |
| gaggtgcgga gaaaaaacct gtacaaagaa ggggacctga cacacttcaa ccagaagctt | 2880 |
| gagggtttca ccttgcccag atgctgggaa gaatgcctag caagctctca gtatcatgct | 2940 |
| cggaagagtg aggttgacaa gttcaacaag gagaattgtt ggaaaaagag aggattgtgc | 3000 |
| ataattccca ccaagtttgg aataagcttt acagttcctt ttctgaatca ggcaggagcc | 3060 |
| ctacttcatg tgtacacaga tggctctgtg ctgctgaccc acgggggac tgagatgggc | 3120 |
| caaggccttc ataccaaaat ggtccaggtg ccagtagac tctgaaaat ccccacctct | 3180 |
| aagatttata tcagcgagac aagcactaac actgtgccca cacctctcc cacggctgcc | 3240 |
| tctgtcagcg ctgacctcaa tggacaggcc gtctatgcgg cttgtcagac catcttgaaa | 3300 |
| aggctggaac cctacaagaa gaagaatccc agtggctcct gggaagactg ggtcacagct | 3360 |
| gcctacatgg acacagtgag cttgtctgcc actgggtttt atagaacacc caatctgggc | 3420 |
| tacagctttg agactaactc agggaacccc ttccactact tcagctatgg ggtggcttgc | 3480 |
| tctgaagtag aaatcgactg cctaacagga gatcataaga acctccgcac agatattgtc | 3540 |
| atggatgttg gctccagtct aaaccctgcc attgatattg acaggtgga aggggcattt | 3600 |
| gtccagggcc ttggcctctt caccctagag gagctacact attcccccga ggggagcctg | 3660 |
| cacacccgtg gccctagcac ctacaagatc ccggcatttg gcagcatccc cattgagttc | 3720 |
| agggtgtccc tgctccgcga ctgccccaac aagaaggcca tctatgcatc gaaggctgtt | 3780 |
| ggagagccgc ccctcttcct ggctgcttct atcttctttg ccatcaaaga tgccatccgt | 3840 |
| gcagctcgag ctcagcacac aggtaataac gtgaaggaac tcttccggct agacagccct | 3900 |
| gccaccccgg agaagatccg caatgcctgc gtggacaagt tcaccaccct gtgtgtcact | 3960 |
| ggtgtcccag aaaactgcaa accctggtct gtgagggtct aa | 4002 |

<210> SEQ ID NO 3
<211> LENGTH: 4002
<212> TYPE: DNA
<213> ORGANISM: Homo sapiens
<220> FEATURE:
<223> OTHER INFORMATION: molybdenum hydroxylase xanthine dehydrogenase
(XDH), xanthine oxidoreductase (XOR), xanthine oxidase (XO)
2211C>T polymorphic site variant allele (exon 21)

<400> SEQUENCE: 3

| | |
|---|---|
| atgacagcag acaaattggt tttctttgtg aatggcagaa aggtggtgga gaaaaatgca | 60 |
| gatccagaga caacccttt ggcctacctg agaagaaagt tggggctgag tggaaccaag | 120 |
| ctcggctgtg agaggggg ctgcggggct tgcacgtga tgctctccaa gtatgatcgt | 180 |
| ctgcagaaca agatcgtcca cttttctgcc aatgcctgcc tggccccat ctgctccttg | 240 |
| caccatgttg cagtgacaac tgtggaagga ataggaagca ccaagacgag gctgcatcct | 300 |
| gtgcaggaga gaattgccaa agccacggc tcccagtgcg ggttctgcac ccctggcatc | 360 |

```
gtcatgagta tgtacacact gctccggaat cagcccgagc ccaccatgga ggagattgag    420
aatgccttcc aaggaaatct gtgccgctgc acaggctaca gacccatcct ccagggcttc    480
cggacctttg ccagggatgg tggatgctgt ggaggagatg ggaataatcc aaattgctgc    540
atgaaccaga agaaagacca ctcagtcagc ctctcgccat ctttattcaa accagaggag    600
ttcacgcccc tggatccaac ccaggagccc atttttcccc cagagttgct gaggctgaaa    660
gacactcctc ggaagcagct gcgatttgaa ggggagcgtg tgacgtggat acaggcctca    720
accctcaagg agctgctgga cctcaaggct cagcaccctg acgccaagct ggtcgtgggg    780
aacacggaga ttggcattga gatgaagttc aagaatatgc tgtttcctat gattgtctgc    840
ccagcctgga tccctgagct gaattcggta gaacatggac ccgacggtat ctcctttgga    900
gctgcttgcc ccctgagcat tgtggaaaaa acccctggtgg atgctgttgc taagcttcct    960
gcccaaaaga cagaggtgtt cagaggggtc ctggagcagc tgcgctggtt tgctgggaag   1020
caagtcaagt ctgtggcgtc cgttggaggg aacatcatca ctgccagccc catctccgac   1080
ctcaaccccg tgttcatggc cagtggggcc aagctgacac ttgtgtccag aggcaccagg   1140
agaactgtcc agatggacca caccttcttc cctggctaca gaaagaccct gctgagcccg   1200
gaggagatac tgctctccat agagatcccc tacagcaggg aggggagta tttctcagca   1260 ttcaagcagg cctcccggag agaagatgac attgccaagg taaccagtgg catgagagtt   1320
ttattcaagc caggaaccac agaggtacag gagctggccc tttgctatgg tggaatggcc   1380
aacagaacca tctcagccct caagaccact cagaggcagc tttccaagct ctggaaggag   1440
gagctgctgc aggacgtgtg tgcaggactg gcagaggagc tgcatctgcc tcccgatgcc   1500
cctggtggca tggtggactt ccggtgcacc ctcaccctca gcttcttctt caagttctac   1560
ctgacagtcc ttcagaagct gggccaagag aacctggaag acaagtgtgg taaactggac   1620
cccactttcg ccagtgcaac tttactgttt cagaaagacc cccagccga tgtccagctc   1680 ttccaagagg tgcccaaggg tcagtctgag gaggacatgg tgggccggcc cctgccccac   1740
ctggcagcgg acatgcaggc ctctggtgag gccgtgtact gtgacgacat tcctcgctac   1800
gagaatgagc tgtctctccg gctggtcacc agcacccggg cccacgccaa gatcaagtcc   1860
atagatacat cagaagctaa gaaggttcca gggtttgttt gtttcatttc cgctgatgat   1920
gttcctggga gtaacataac tggaatttgt aatgatgaga cagtctttgc gaaggataag   1980
gttacttgtg ttgggcatat cattggtgct gtggttgctg acaccccgga acacacacag   2040
agagctgccc aagggggtgaa aatcacctat gaagaactac cagccattat cacaattgag   2100
gatgctataa agaacaactc ctttatgga cctgagctga gatcgagaa aggggaccta   2160 aagaagggt tttccgaagc agataatgtt gtgtcagggg agatatacat tggtggccaa   2220
gagcacttct acctggagac tcactgcacc attgctgttc caaaaggcga ggcaggggag   2280
atggagctct ttgtgtctac acagaacacc atgaagaccc agagctttgt tgcaaaaatg   2340 ttggggggttc cagcaaaccg gattgtggtt cgagtgaaga aatgggagg aggctttgga   2400 ggcaaggaga cccggagcac tgtggtgtcc acggcagtgg ccctggctgc atataagacc   2460
ggccgccctg tgcgatgcat gctggaccgt gatgaggaca tgctgataac tggtggcaga   2520 catccccttcc tggccagata caaggttggc ttcatgaaga ctgggacagt tgtggctctt   2580
gaggtggacc acttcagcaa tgtggggaac acccaggatc tctctcagag tattatggaa   2640 cgagcttttat tccacatgga caactgctat aaaaatccca acatccgggg cactgggcgg   2700
ctgtgcaaaa ccaaccttcc ctccaacacg gccttccggg gctttggggg gccccagggg   2760
```

```
atgctcattg ccgagtgctg gatgagtgaa gttgcagtga cctgtgggat gcctgcagag      2820
gaggtgcgga gaaaaaacct gtacaaagaa ggggacctga cacacttcaa ccagaagctt      2880
gagggtttca ccttgcccag atgctgggaa gaatgcctag caagctctca gtatcatgct      2940
cggaagagtg aggttgacaa gttcaacaag gagaattgtt ggaaaaagag aggattgtgc      3000
ataattccca ccaagtttgg aataagcttt acagttcctt ttctgaatca ggcaggagcc      3060
ctacttcatg tgtacacaga tggctctgtg ctgctgaccc acgggggac tgagatgggc       3120 caaggccttc ataccaaaat ggtccaggtg ccagtagag ctctgaaaat ccccacctct        3180
aagatttata tcagcgagac aagcactaac actgtgccca cacctctcc cacggctgcc       3240 tctgtcagcg ctgaccctcaa tggacaggcc gtctatgcgg cttgtcagac catcttgaaa     3300
aggctggaac cctacaagaa gaagaatccc agtggctcct gggaagactg ggtcacagct      3360
gcctacatgg acacagtgag cttgtctgcc actgggtttt atagaacacc caatctgggc      3420
tacagctttg agactaactc agggaacccc ttccactact tcagctatgg ggtggcttgc      3480
tctgaagtag aaatcgactg cctaacagga gatcataaga acctccgcac agatattgtc      3540
atggatgttg ctccagtct aaaccctgcc attgatattg acaggtgga aggggcattt        3600 gtccagggcc ttggcctctt caccctagag gagctacact attcccccga ggggagcctg      3660
cacacccgtg gccctagcac ctacaagatc ccggcatttg gcagcatccc cattgagttc      3720
agggtgtccc tgctccgcga ctgccccaac aagaaggcca tctatgcatc gaaggctgtt      3780
ggagagccgc ccctcttcct ggctgcttct atcttctttg ccatcaaaga tgccatccgt      3840
gcagctcgag ctcagcacac aggtaataac gtgaaggaac tcttccggct agacagccct      3900
gccaccccgg agaagatccg caatgcctgc gtggacaagt tcaccaccct gtgtgtcact      3960
ggtgtcccag aaaactgcaa accctggtct gtgagggtct aa                        4002
```

<210> SEQ ID NO 4
<211> LENGTH: 4002
<212> TYPE: DNA
<213> ORGANISM: Homo sapiens
<220> FEATURE:
<223> OTHER INFORMATION: molybdenum hydroxylase xanthine dehydrogenase
      (XDH), xanthine oxidoreductase (XOR), xanthine oxidase (XO)
      3030T>C polymorphic site variant allele (exon 27)

<400> SEQUENCE: 4

```
atgacagcag acaaattggt tttctttgtg aatggcagaa aggtggtgga gaaaaatgca       60
gatccagaga caacccttttt ggcctacctg agaagaaagt tggggctgag tggaaccaag      120
ctcggctgtg gagagggggg ctgcggggct tgcacagtga tgctctccaa gtatgatcgt      180
ctgcagaaca agatcgtcca cttttctgcc aatgcctgcc tggcccccat ctgctccttg      240
caccatgttg cagtgacaac tgtggaagga ataggaagca ccaagacgag gctgcatcct      300
gtgcaggaga gaattgccaa agccacggc tcccagtgcg ggttctgcac ccctggcatc       360
gtcatgagta tgtacacact gctccggaat cagcccgagc ccaccatgga ggagattgag      420
aatgccttcc aaggaaatct gtgccgctgc acaggctaca gacccatcct ccagggcttc      480
cggacctttg ccaggatgg tggatgctgt ggaggagatg gaataatcc aaattgctgc        540 atgaaccaga gaaagacca ctcagtcagc ctctcgccat ctttattcaa accagaggag      600
ttcacgcccc tggatccaac ccaggagccc attttcccc agagttgct gaggctgaaa       660 gacactcctc ggaagcagct gcgatttgaa ggggagcgtg tgacgtggat acaggcctca      720
accctcaagg agctgctgga cctcaaggct cagcaccctg acgccaagct ggtcgtgggg      780
```

```
aacacggaga ttggcattga gatgaagttc aagaatatgc tgtttcctat gattgtctgc    840
ccagcctgga tccctgagct gaattcggta gaacatggac ccgacggtat ctcctttgga    900
gctgcttgcc ccctgagcat tgtggaaaaa accctggtgg atgctgttgc taagcttcct    960
gcccaaaaga cagaggtgtt cagaggggtc ctggagcagc tgcgctggtt tgctgggaag   1020
caagtcaagt ctgtggcgtc cgttggaggg aacatcatca ctgccagccc catctccgac   1080
ctcaaccccg tgttcatggc cagtggggcc aagctgacac ttgtgtccag aggcaccagg   1140
agaactgtcc agatggacca caccttcttc cctggctaca gaaagaccct gctgagcccg   1200
gaggagatac tgctctccat agagatcccc tacagcaggg aggggagta tttctcagca   1260 ttcaagcagg cctcccggag agaagatgac attgccaagg taaccagtgg catgagagtt   1320
ttattcaagc caggaaccac agaggtacag gagctggccc tttgctatgg tggaatggcc   1380
aacagaacca tctcagccct caagaccact cagaggcagc tttccaagct ctggaaggag   1440
gagctgctgc aggacgtgtg tgcaggactg gcagaggagc tgcatctgcc tcccgatgcc   1500
cctggtggca tggtggactt ccggtgcacc ctcaccctca gcttcttctt caagttctac   1560
ctgacagtcc ttcagaagct gggccaagag aacctggaag acaagtgtgg taaactggac   1620
cccactttcg ccagtgcaac tttactgttt cagaaagacc ccccagccga tgtccagctc   1680
ttccaagagg tgcccaaggg tcagtctgag gaggacatgg tgggccggcc cctgccccac   1740
ctggcagcgg acatgcaggc ctctggtgag gccgtgtact gtgacgacat tcctcgctac   1800
gagaatgagc tgtctctccg gctggtcacc agcacccggg cccacgccaa gatcaagtcc   1860
atagatacat cagaagctaa gaaggttcca gggtttgttt gtttcatttc cgctgatgat   1920
gttcctggga gtaacataac tggaatttgt aatgatgaga cagtctttgc gaaggataag   1980
gttacttgtg ttgggcatat cattggtgct gtggttgctg acaccccgga acacacacag   2040
agagctgccc aaggggtgaa aatcacctat gaagaactac cagccattat cacaattgag   2100
gatgctataa agaacaactc ctttttatgga cctgagctga agatcgagaa aggggaccta   2160 aagaagggt tttccgaagc agataatgtt gtgtcagggg agatatacat cggtggccaa   2220
gagcacttct acctggagac tcactgcacc attgctgttc caaaaggcga ggcaggggag   2280
atggagctct ttgtgtctac acagaacacc atgaagaccc agagctttgt tgcaaaaatg   2340
ttgggggttc cagcaaaccg gattgtggtt cgagtgaaga gaatgggagg aggctttgga   2400
ggcaaggaga cccggagcac tgtggtgtcc acggcagtgg ccctggctgc atataagacc   2460
ggccgccctg tgcgatgcat gctggaccgt gatgaggaca tgctgataac tggtggcaga   2520
catcccttcc tggccagata caaggttggc ttcatgaaga ctgggacagt tgtggctctt   2580
gaggtggacc acttcagcaa tgtggggaac acccaggatc tctctcagag tattatggaa   2640
cgagctttat tccacatgga caactgctat aaaatcccca acatccgggg cactgggcgg   2700
ctgtgcaaaa ccaaccttcc ctccaacacg gccttccggg gctttggggg gccccagggg   2760
atgctcattg ccgagtgctg gatgagtgaa gttgcagtga cctgtgggat gcctgcagag   2820
gaggtgcgga gaaaaaacct gtacaaagaa ggggacctga cacacttcaa ccagaagctt   2880
gagggtttca ccttgcccag atgctgggaa gaatgcctag caagctctca gtatcatgct   2940
cggaagagtg aggttgacaa gttcaacaag gagaattgtt ggaaaagag aggattgtgc   3000 ataattccca ccaagtttgg aataagcttc acagttcctt ttctgaatca ggcaggagcc   3060
ctacttcatg tgtacacaga tggctctgtg ctgctgaccc acgggggggac tgagatgggc   3120 caaggccttc ataccaaaat ggtccaggtg gccagtagag ctctgaaaat ccccaccctct  3180
```

```
aagatttata tcagcgagac aagcactaac actgtgccca acacctctcc cacggctgcc    3240
tctgtcagcg ctgacctcaa tggacaggcc gtctatgcgg cttgtcagac catcttgaaa    3300
aggctggaac cctacaagaa gaagaatccc agtggctcct gggaagactg ggtcacagct    3360
gcctacatgg acacagtgag cttgtctgcc actgggtttt atagaacacc caatctgggc    3420
tacagctttg agactaactc agggaacccc ttccactact tcagctatgg ggtggcttgc    3480
tctgaagtag aaatcgactg cctaacagga gatcataaga acctccgcac agatattgtc    3540
atggatgttg gctccagtct aaaccctgcc attgatattg gacaggtgga aggggcattt    3600
gtccagggcc ttggcctctt caccctagag gagctacact attcccccga ggggagcctg    3660
cacacccgtg gccctagcac ctacaagatc ccggcatttg gcagcatccc cattgagttc    3720
agggtgtccc tgctccgcga ctgccccaac aagaaggcca tctatgcatc gaaggctgtt    3780
ggagagccgc ccctcttcct ggctgcttct atcttctttg ccatcaaaga tgccatccgt    3840
gcagctcgag ctcagcacac aggtaataac gtgaaggaac tcttccggct agacagccct    3900
gccaccccgg agaagatccg caatgcctgc gtggacaagt tcaccaccct gtgtgtcact    3960
ggtgtcccag aaaactgcaa accctggtct gtgagggtct aa                       4002
```

<210> SEQ ID NO 5
<211> LENGTH: 4002
<212> TYPE: DNA
<213> ORGANISM: Homo sapiens
<220> FEATURE:
<223> OTHER INFORMATION: molybdenum hydroxylase xanthine dehydrogenase
       (XDH), xanthine oxidoreductase (XOR), xanthine oxidase (XO)
       837C>T polymorphic site variant allele (exon 10)

<400> SEQUENCE: 5

```
atgacagcag acaaattggt tttctttgtg aatggcagaa aggtggtgga gaaaaatgca      60
gatccagaga caaccctttt ggcctacctg agaagaaagt tggggctgag tggaaccaag     120
ctcggctgtg agaggggggg ctgcggggct tgcacagtga tgctctccaa gtatgatcgt     180
ctgcagaaca agatcgtcca cttttctgcc aatgcctgcc tggcccccat ctgtccttg     240 caccatgttg cagtgacaac tgtggaagga ataggaagca ccaagacgag gctgcatcct     300
gtgcaggaga gaattgccaa aagccacggc tcccagtgcg ggttctgcac ccctggcatc     360
gtcatgagta tgtacacact gctccggaat cagcccgagc ccaccatgga ggagattgag     420
aatgccttcc aaggaaatct gtgccgctgc acaggctaca gacccatcct ccagggcttc     480
cggacctttg ccagggatgg tggatgctgt ggaggagatg ggaataatcc aaattgctgc     540
atgaaccaga gaaagaccca ctcagtcagc ctctcgccat ctttattcaa accagaggag     600
ttcacgcccc tggatccaac ccaggagccc attttttcccc cagagttgct gaggctgaaa     660
gacactcctc ggaagcagct gcgatttgaa ggggagcgtg tgacgtggat acaggcctca     720 acccctcaagg agctgctgga cctcaaggct cagcaccctg acgccaagct ggtcgtgggg     780
aacacgagga ttggcattga gatgaagttc aagaatatgc tgtttcctat gattgtttgc     840
ccagcctgga tccctgagct gaattcggta gaacatggac ccgacggtat ctcctttgga     900
gctgcttgcc ccctgagcat tgtggaaaaa accctggtgg atgctgttgc taagcttcct     960
gcccaaaaga cagaggtgtt cagaggggtc ctggagcagc tgcgctggtt tgctgggaag    1020
caagtcaagt ctggcgtc cgttggaggg aacatcatca ctgccagccc catctccgac    1080
ctcaaccccg tgttcatggc cagtgggggcc aagctgacac ttgtgtccag aggcaccagg    1140
agaactgtcc agatggacca caccttcttc cctggctaca gaaagaccct gctgagcccg    1200
```

```
gaggagatac tgctctccat agagatcccc tacagcaggg aggggagta tttctcagca    1260 ttcaagcagg cctcccggag agaagatgac attgccaagg taaccagtgg catgagagtt    1320
ttattcaagc caggaaccac agaggtacag gagctggccc tttgctatgg tggaatggcc    1380
aacagaacca tctcagccct caagaccact cagaggcagc tttccaagct ctggaaggag    1440
gagctgctgc aggacgtgtg tgcaggactg gcagaggagc tgcatctgcc tcccgatgcc    1500
cctggtggca tggtggactt ccggtgcacc ctcaccctca gcttcttctt caagttctac    1560
ctgacagtcc ttcagaagct gggccaagag aacctggaag acaagtgtgg taaactggac    1620
cccactttcg ccagtgcaac tttactgttt cagaaagacc cccagccga tgtccagctc    1680 ttccaagagg tgcccaaggg tcagtctgag gaggacatgg tgggccggcc cctgccccac    1740
ctggcagcgg acatgcaggc ctctggtgag gccgtgtact gtgacgacat tcctcgctac    1800
gagaatgagc tgtctctccg gctggtcacc agcacccggg cccacgccaa gatcaagtcc    1860
atagatacat cagaagctaa gaaggttcca gggtttgttt gtttcatttc cgctgatgat    1920
gttcctggga gtaacataac tggaatttgt aatgatgaga cagtctttgc gaaggataag    1980
gttacttgtg ttgggcatat cattggtgct gtggttgctg acaccccgga acacacacag    2040
agagctgccc aagggtgaa atcacctat gaagaactac cagccattat cacaattgag    2100
gatgctataa agaacaactc cttttatgga cctgagctga agatcgagaa aggggaccta    2160 aagaagggt tttccgaagc agataatgtt gtgtcagggg agatatacat cggtggccaa    2220
gagcacttct acctggagac tcactgcacc attgctgttc caaaggcga ggcaggggag    2280 atggagctct ttgtgtctac acagaacacc atgaagaccc agagctttgt tgcaaaaatg    2340
ttgggggttc cagcaaaccg gattgtggtt cgagtgaaga aatgggagg aggctttgga    2400 ggcaaggaga cccggagcac tgtggtgtcc acggcagtgg ccctggctgc atataagacc    2460
ggccgccctg tgcgatgcat gctggaccgt gatgaggaca tgctgataac tggtggcaga    2520
catcccttcc tggccagata caaggttggc ttcatgaaga ctgggacagt tgtggctctt    2580
gaggtggacc acttcagcaa tgtggggaac acccaggatc tctctcagag tattatggaa    2640
cgagctttat tccacatgga caactgctat aaaatcccca acatcggggg cactgggcgg    2700
ctgtgcaaaa ccaaccttcc ctccaacacg gccttccggg gctttggggg gccccagggg    2760
atgctcattg ccgagtgctg gatgagtgaa gttgcagtga cctgtgggat gcctgcagag    2820
gaggtgcgga aaaaaacct gtacaaagaa ggggacctga cacacttcaa ccagaagctt    2880
gagggtttca ccttgcccag atgctgggaa gaatgcctag caagctctca gtatcatgct    2940
cggaagagtg aggttgacaa gttcaacaag gagaattgtt ggaaaaagag aggattgtgc    3000
ataattccca ccaagtttgg aataagcttt acagttcctt ttctgaatca ggcaggagcc    3060
ctacttcatg tgtacacaga tggctctgtg ctgctgaccc acggggggac tgagatgggc    3120
caaggccttc ataccaaaat ggtccaggtg ccagtagag ctctgaaaat ccccacctct    3180
aagatttata tcagcgagac aagcactaac actgtgccca cacctctcc cacggctgcc    3240 tctgtcagcg ctgacctcaa tggacaggcc gtctatgcgg cttgtcagac catcttgaaa    3300
aggctggaac cctacaagaa gaagaatccc agtggctcct gggaagactg gtcacagct    3360 gcctacatgg acacagtgag cttgtctgcc actgggtttt atagaacacc caatctgggc    3420
tacagctttg agactaactc agggaacccc ttccactact tcagctatgg ggtggcttgc    3480
tctgaagtag aaatcgactg cctaacagga gatcataaga acctccgcac agatattgtc    3540
atggatgttg ctccagtctc aaaccctgcc attgatattg acaggtgga agggcatttt    3600
```

```
gtccagggcc ttggcctctt caccctagag gagctacact attccccccga gggagcctg    3660 cacacccgtg gccctagcac ctacaagatc ccggcatttg cagcatccc cattgagttc    3720 agggtgtccc tgctccgcga ctgccccaac aagaaggcca tctatgcatc gaaggctgtt    3780
ggagagccgc ccctcttcct ggctgcttct atcttctttg ccatcaaaga tgccatccgt    3840
gcagctcgag ctcagcacac aggtaataac gtgaaggaac tcttccggct agacagccct    3900
gccaccccgg agaagatccg caatgcctgc gtggacaagt tcaccaccct gtgtgtcact    3960
ggtgtcccag aaaactgcaa accctggtct gtgagggtct aa                       4002

<210> SEQ ID NO 6
<211> LENGTH: 4002
<212> TYPE: DNA
<213> ORGANISM: Homo sapiens
<220> FEATURE:
<223> OTHER INFORMATION: molybdenum hydroxylase xanthine dehydrogenase
      (XDH), xanthine oxidoreductase (XOR), xanthine oxidase (XO)
      3717G>A polymorphic site variant allele (exon 34)

<400> SEQUENCE: 6
atgacagcag acaaattggt tttctttgtg aatggcagaa aggtggtgga gaaaaatgca    60
gatccagaga caaccctttt ggcctacctg agaagaaagt tggggctgag tggaaccaag    120
ctcggctgtg gagagggggg ctgcggggct gcacagtga tgctctccaa gtatgatcgt     180
ctgcagaaca agatcgtcca cttttctgcc aatgcctgcc tggcccccat ctgctccttg    240
caccatgttg cagtgacaac tgtggaagga ataggaagca ccaagacgag gctgcatcct    300
gtgcaggaga gaattgccaa aagccacggc tcccagtgcg gttctgcac ccctggcatc     360 gtcatgagta tgtacacact gctccggaat cagcccgagc ccaccatgga ggagattgag    420
aatgccttcc aaggaaatct gtgccgctgc acaggctaca gacccatcct ccagggcttc    480
cggacctttg ccagggatgg tggatgctgt ggaggagatg ggataatcc aaattgctgc    540 atgaaccaga gaaagacca ctcagtcagc ctctcgccat ctttattcaa accagaggag     600
ttcacgcccc tggatccaac ccaggagccc attttcccc cagagttgct gaggctgaaa     660
gacactcctc ggaagcagct gcgatttgaa ggggagcgtg tgacgtggat acaggcctca    720
accctcaagg agctgctgga cctcaaggct cagcaccctg acgccaagct ggtcgtgggg    780
aacacggaga ttggcattga tgaagttc aagaatatgc tgtttcctat gattgtctgc     840
ccagcctgga tccctgagct gaattcggta gaacatggac ccgacggtat ctcctttgga    900
gctgcttgcc ccctgagcat tgtggaaaaa accctggtgg atgctgttgc taagcttcct    960
gcccaaaaga cagaggtgtt cagagggtc ctggagcagc tgcgctggtt tgctgggaag    1020
caagtcaagt ctgtggcgtc cgttggaggg aacatcatca ctgccagccc catctccgac    1080
ctcaaccccg tgttcatggc cagtgggcc aagctgacac ttgtgtccag aggcaccagg    1140
agaactgtcc agatggacca caccttcttc cctggctaca aaagaccct gctgagcccg    1200 gaggagatac tgctctccat agagatcccc tacagcaggg aggggagta tttctcagca    1260 ttcaagcagg cctcccggag agaagatgac attgccaagg taaccagtgg catgagagtt    1320
ttattcaagc caggaaccac agaggtacag gagctggccc tttgctatgg tggaatggcc    1380
aacagaacca tctcagccct caagaccact cagaggcagc tttccaagct ctggaaggag    1440
gagctgctgc aggacgtgtg tgcaggactg gcagaggagc tgcatctgcc tccgatgcc    1500 cctggtggca tggtggactt ccggtgcacc ctcaccctca gcttcttctt caagttctac    1560
ctgacagtcc ttcagaagct gggccaagag aacctggaag acaagtgtgg taaactggac    1620
```

```
cccactttcg ccagtgcaac tttactgttt cagaaagacc ccccagccga tgtccagctc    1680
ttccaagagg tgcccaaggg tcagtctgag gaggacatgg tgggccggcc cctgccccac    1740
ctggcagcgg acatgcaggc ctctggtgag gccgtgtact gtgacgacat tcctcgctac    1800
gagaatgagc tgtctctccg gctggtcacc agcacccggg cccacgccaa gatcaagtcc    1860
atagatacat cagaagctaa gaaggttcca gggtttgttt gtttcatttc cgctgatgat    1920
gttcctggga gtaacataac tggaatttgt aatgatgaga cagtctttgc gaaggataag    1980
gttacttgtg ttgggcatat cattggtgct gtggttgctg acaccccgga acacacacag    2040
agagctgccc aagggtgaa  aatcacctat gaagaactac cagccattat cacaattgag    2100
gatgctataa agaacaactc ctttatgga  cctgagctga agatcgagaa agggggccta    2160 aagaagggt  tttccgaagc agataatgtt gtgtcagggg agatatacat cggtggccaa    2220
gagcacttct acctggagac tcactgcacc attgctgttc caaaggcga  ggcaggggag    2280 atggagctct ttgtgtctac acagaacacc atgaagaccc agagctttgt tgcaaaaatg    2340 ttggggggttc cagcaaaccg gattgtggtt cgagtgaaga aatgggagg  aggctttgga    2400 ggcaaggaga cccggagcac tgtggtgtcc acggcagtgg ccctggctgc atataagacc    2460
ggccgccctg tgcgatgcat gctggaccgt gatgaggaca tgctgataac tggtggcaga    2520 catccctttcc tggccagata caaggttggc ttcatgaaga ctgggacagt tgtggctctt    2580
gaggtggacc acttcagcaa tgtggggaac acccaggatc tctctcagag tattatggaa    2640
cgagctttat tccacatgga caactgctat aaaatcccca acatccgggg cactgggcgg    2700
ctgtgcaaaa ccaaccttcc ctccaacacg gccttccggg gctttggggg gccccagggg    2760
atgctcattg ccgagtgctg gatgagtgaa gttgcagtga cctgtgggat gcctgcagag    2820
gaggtgcgga gaaaaaacct gtacaaagaa ggggacctga cacacttcaa ccagaagctt    2880 gagggttttca ccttgcccag atgctgggaa gaatgcctag caagctctca gtatcatgct    2940
cggaagagtg aggttgacaa gttcaacaag gagaattgtt ggaaaaagag aggattgtgc    3000
ataattccca ccaagtttgg aataagcttt acagttcctt ttctgaatca ggcaggagcc    3060
ctacttcatg tgtacacaga tggctctgtg ctgctgaccc acgggggac  tgagatgggc    3120 caaggccttc ataccaaaat ggtccaggtg gccagtagag ctctgaaaat ccccaccctct    3180 aagatttata tcagcgagac aagcactaac actgtgccca cacctctcc  cacggctgcc    3240 tctgtcagcg ctgacctcaa tggacaggcc gtctatgcgg cttgtcagac catcttgaaa    3300
aggctggaac cctacaagaa gaagaatccc agtggctcct gggaagactg ggtcacagct    3360
gcctacatgg acacagtgag cttgtctgcc actgggtttt atagaacacc caatctgggc    3420
tacagctttg agactaactc agggaacccc ttccactact tcagctatgg ggtggcttgc    3480
tctgaagtag aaatcgactg cctaacagga gatcataaga acctccgcac agatattgtc    3540
atggatgttg gctccagtct aaaccctgcc attgatattg acaggtgga  agggcatttt    3600 gtccagggcc ttggcctctt caccctagag gagctacact attccccga  ggggagcctg    3660 cacacccgtg gccctagcac ctacaagatc ccggcatttg gcagcatccc cattgaattc    3720
agggtgtccc tgctccgcga ctgccccaac aagaaggcca tctatgcatc gaaggctgtt    3780
ggagagccgc ccctcttcct ggctgcttct atcttctttg ccatcaaaga tgccatccgt    3840
gcagctcgag ctcagcacac aggtaataac gtgaaggaac tcttccggct agacagccct    3900
gccacccccg agaagatccg caatgcctgc gtggacaagt tcaccaccct gtgtgtcact    3960
ggtgtcccag aaaactgcaa accctggtct gtgagggtct aa                       4002
```

<210> SEQ ID NO 7
<211> LENGTH: 4002
<212> TYPE: DNA
<213> ORGANISM: Homo sapiens
<220> FEATURE:
<223> OTHER INFORMATION: molybdenum hydroxylase xanthine dehydrogenase
(XDH), xanthine oxidoreductase (XOR), xanthine oxidase (XO)
2107A>G polymorphic site variant allele (exon 20)

<400> SEQUENCE: 7

```
atgacagcag acaaattggt tttctttgtg aatggcagaa aggtggtgga gaaaaatgca      60
gatccagaga caacccttt ggcctacctg agaagaaagt tggggctgag tggaaccaag     120
ctcggctgtg gagaggggg ctgcggggct tgcacagtga tgctctccaa gtatgatcgt     180
ctgcagaaca agatcgtcca cttttctgcc aatgcctgcc tggcccccat ctgctccttg    240
caccatgttg cagtgacaac tgtgaagga ataggaagca ccaagacgag gctgcatcct    300
gtgcaggaga gaattgccaa agccacggc tcccagtgcg ggttctgcac ccctggcatc    360
gtcatgagta tgtacacact gctccggaat cagcccgagc ccaccatgga ggagattgag    420
aatgccttcc aaggaaatct gtgccgctgc acaggctaca gacccatcct ccagggcttc    480
cggacctttg ccagggatgg tggatgctgt ggaggagatg ggaataatcc aaattgctgc    540
atgaaccaga gaaagacca ctcagtcagc ctctcgccat ctttattcaa accagaggag    600
ttcacgcccc tggatccaac ccaggagccc attttccc cagagttgct gaggctgaaa     660
gacactcctc ggaagcagct gcgatttgaa ggggagcgtg tgacgtggat acaggcctca    720
accctcaagg agctgctgga cctcaaggct cagcaccctg acgccaagct ggtcgtgggg    780
aacacggaga ttggcattga gatgaagttc aagaatatgc tgtttcctat gattgtctgc    840
ccagcctgga tccctgagct gaattcggta gaacatggac ccgacggtat ctccttggga    900
gctgcttgcc ccctgagcat tgtgaaaaa accctggtgg atgctgttgc taagcttcct    960
gcccaaaaga cagaggtgtt cagaggggtc ctggagcagc tgcgctggtt tgctgggaag   1020
caagtcaagt ctgtggcgtc cgttggaggg aacatcatca ctgccagccc catctccgac   1080
ctcaaccccg tgttcatggc cagtgggggcc aagctgacac ttgtgtccag aggcaccagg   1140
agaactgtcc agatggacca caccttcttc cctggctaca gaaagaccct gctgagcccg   1200
gaggagatac tgctctccat agagatcccc tacagcaggg aggggagta tttctcagca   1260
ttcaagcagg cctcccggag agaagatgac attgccaagg taaccagtgg catgagagtt   1320
ttattcaagc caggaaccac agaggtacag gagctggccc tttgctatgg tggaatggcc   1380
aacagaacca tctcagccct caagaccact cagaggcagc tttccaagct ctggaaggag   1440
gagctgctgc aggacgtgtg tgcaggactg gcagaggagc tgcatctgcc tcccgatgcc   1500
cctggtggca tggtggactt ccggtgcacc ctcacccctc gcttcttctt caagttctac   1560
ctgacagtcc ttcagaagct gggccaagag aacctggaag acaagtgtgg taaactggac   1620
cccactttcg ccagtgcaac tttactgttt cagaaagacc ccccagccga tgtccagctc   1680
ttccaagagg tgcccaaggg tcagtctgag gaggacatgt gggccggcc cctgccccac   1740
ctggcagcgg acatgcaggc ctctggtgag gccgtgtact gtgacgacat tcctcgctac   1800
gagaatgagc tgtctctccg gctggtcacc agcacccggg cccacgccaa gatcaagtcc   1860
atagatacat cagaagctaa gaaggttcca gggtttgttt gtttcatttc cgctgatgat   1920
gttcctggga gtaacataac tggaatttgt aatgatgaga cagtctttgc gaaggataag   1980
gttacttgtg ttgggcatat cattggtgct gtggttgctg acacccccgga acacacacag   2040
```

```
agagctgccc aagggggtgaa atcacctat gaagaactac cagccattat cacaattgag    2100
gatgctgtaa agaacaactc cttttatgga cctgagctga agatcgagaa aggggaccta    2160 aagaagggggt tttccgaagc agataatgtt gtgtcagggg agatatacat cggtggccaa   2220
gagcacttct acctggagac tcactgcacc attgctgttc caaaaggcga ggcaggggag    2280
atggagctct ttgtgtctac acagaacacc atgaagaccc agagctttgt tgcaaaaatg    2340
ttgggggttc cagcaaaccg gattgtggtt cgagtgaaga gaatgggagg aggctttgga    2400
ggcaaggaga cccggagcac tgtggtgtcc acggcagtgg ccctggctgc atataagacc    2460
ggccgccctg tgcgatgcat gctggaccgt gatgaggaca tgctgataac tggtggcaga    2520
catcccttcc tggccagata caaggttggc ttcatgaaga ctgggacagt tgtggctctt    2580
gaggtggacc acttcagcaa tgtggggaac acccaggatc tctctcagag tattatggaa    2640
cgagctttat tccacatgga caactgctat aaaatcccca acatccgggg cactgggcgg    2700
ctgtgcaaaa ccaaccttcc ctccaacacg gccttccggg gctttggggg cccccagggg    2760
atgctcattg ccgagtgctg gatgagtgaa gttgcagtga cctgtgggat gcctgcagag    2820
gaggtgcgga gaaaaaacct gtacaaagaa ggggacctga cacacttcaa ccagaagctt    2880
gagggtttca ccttgcccag atgctgggaa gaatgcctag caagctctca gtatcatgct    2940
cggaagagtg aggttgacaa gttcaacaag gagaattgtt ggaaaaagag aggattgtgc    3000
ataattccca ccaagtttgg aataagcttt acagttcctt ttctgaatca ggcaggagcc    3060
ctacttcatg tgtacacaga tggctctgtg ctgctgaccc acggggggac tgagatgggc    3120
caaggccttc ataccaaaat ggtccaggtg gccagtagag ctctgaaaat ccccacctct    3180
aagatttata tcagcgagac aagcactaac actgtgccca cacctctccc cacggctgcc    3240
tctgtcagcg ctgacctcaa tggacaggcc gtctatgcgg cttgtcagac catcttgaaa    3300
aggctggaac cctacaagaa gaagaatccc agtggctcct gggaagactg ggtcacagct    3360
gcctacatgg acacagtgag cttgtctgcc actgggtttt atagaacacc caatctgggc    3420
tacagctttg agactaactc agggaacccc ttccactact tcagctatgg ggtggcttgc    3480
tctgaagtag aaatcgactg cctaacagga gatcataaga acctccgcac agatattgtc    3540
atggatgttg gctccagtct aaaccctgcc attgatattg acaggtggga aggggcattt    3600
gtccagggcc ttggcctctt cacccctagag gagctacact attcccccga ggggagcctg    3660
cacacccgtg gccctagcac ctacaagatc ccggcatttg gcagcatccc cattgagttc    3720
agggtgtccc tgctccgcga ctgccccaac aagaaggcca tctatgcatc gaaggctgtt    3780
ggagagccgc ccctcttcct ggctgcttct atcttctttg ccatcaaaga tgccatccgt    3840
gcagctcgag ctcagcacac aggtaataac gtgaaggaac tcttccggct agacagccct    3900
gccaccccgg agaagatccg caatgcctgc gtggacaagt tcaccaccct gtgtgtcact    3960
ggtgtcccag aaaactgcaa accctggtct gtgagggtct aa                       4002
```

<210> SEQ ID NO 8
<211> LENGTH: 4002
<212> TYPE: DNA
<213> ORGANISM: Homo sapiens
<220> FEATURE:
<223> OTHER INFORMATION: molybdenum hydroxylase xanthine dehydrogenase
    (XDH), xanthine oxidoreductase (XOR), xanthine oxidase (XO)
    1936A>G polymorphic site variant allele (exon 18)

<400> SEQUENCE: 8

```
atgacagcag acaaattggt tttctttgtg aatggcagaa aggtggtgga gaaaaatgca    60
```

```
gatccagaga caacccttttt ggcctacctg agaagaaagt tggggctgag tggaaccaag    120
ctcggctgtg gagaggggggg ctgcggggct tgcacagtga tgctctccaa gtatgatcgt    180
ctgcagaaca agatcgtcca cttttctgcc aatgcctgcc tggcccccat ctgctccttg    240
caccatgttg cagtgacaac tgtggaagga ataggaagca ccaagacgag gctgcatcct    300
gtgcaggaga gaattgccaa aagccacggc tcccagtgcg ggttctgcac cctggcatc     360 gtcatgagta tgtacacact gctccggaat cagcccgagc ccaccatgga ggagattgag    420
aatgccttcc aaggaaatct gtgccgctgc acaggctaca gacccatcct ccagggcttc    480
cggacctttg ccagggatgg tggatgctgt ggaggagatg ggaataatcc aaattgctgc    540
atgaaccaga agaaagacca ctcagtcagc ctctcgccat ctttattcaa accagaggag    600
ttcacgcccc tggatccaac ccaggagccc attttttcccc cagagttgct gaggctgaaa    660
gacactcctc ggaagcagct gcgatttgaa ggggagcgtg tgacgtggat acaggcctca    720 acctcaagg agctgctgga cctcaaggct cagcaccctg acgccaagct ggtcgtgggg     780
aacacggaga ttggcattga gatgaagttc aagaatatgc tgtttcctat gattgtctgc    840
ccagcctgga tccctgagct gaattcggta aacatggac ccgacggtat ctcctttgga     900
gctgcttgcc ccctgagcat tgtggaaaaa accctggtgg atgctgttgc taagcttcct    960
gcccaaaaga cagaggtgtt cagaggggtc ctggagcagc tgcgctggtt tgctgggaag   1020
caagtcaagt ctgtggcgtc cgttggaggg aacatcatca ctgccagccc catctccgac   1080
ctcaaccccg tgttcatggc cagtggggcc aagctgacac ttgtgtccag aggcaccagg   1140
agaactgtcc agatggacca caccttcttc cctggctaca gaaagaccct gctgagcccg   1200
gaggagatac tgctctccat agagatcccc tacagcaggg aggggagta tttctcagca   1260 ttcaagcagg cctcccggag agaagatgac attgccaagg taaccagtgg catgagagtt   1320
ttattcaagc caggaaccac agaggtacag gagctggccc tttgctatgg tggaatggcc   1380
aacagaacca tctcagccct caagaccact cagaggcagc tttccaagct ctggaaggag   1440
gagctgctgc aggacgtgtg tgcaggactg gcagaggagc tgcatctgcc tcccgatgcc   1500
cctggtggca tggtggactt ccggtgcacc ctcaccctca gcttcttctt caagttctac   1560 ctgcagtcc ttcagaagct gggccaagag aacctggaag acaagtgtgg taaactggac   1620 cccacttcg ccagtgcaac tttactgttt cagaaagacc cccagccga tgtccagctc    1680 ttccaagagt gcccaagggg tcagtctgag gaggacatgg tgggccggcc cctgcccac   1740 ctggcagcgg acatgcaggc ctctggtgag gccgtgtact gtgacgacat tcctcgctac   1800
gagaatgagc tgtctctccg gctggtcacc agcacccggg cccacgccaa gatcaagtcc   1860
atagatacat cagaagctaa gaaggttcca gggtttgttt gtttcatttc cgctgatgat   1920
gttcctggga gtaacgtaac tggaatttgt aatgatgaga cagtcttttgc gaaggataag   1980 gttacttgtg ttgggcatat cattggtgct gtggttgctg acaccccgga acacacacag   2040
agagctgccc aagggggtgaa atcacctat gaagaactac cagccattat cacaattgag   2100
gatgctataa agaacaactc ctttttatgga cctgagctga gatcgagaa aggggaccta   2160 aagaagggt tttccgaagc agataatgtt gtgtcagggg agatatacat cggtggccaa   2220
gagcacttct acctggagac tcactgcacc attgctgttc caaaggcga ggcagggag    2280 atggagctct ttgtgtctac acagaacacc atgaagaccc agagctttgt tgcaaaaatg   2340 ttggggggttc cagcaaaccg gattgtggtt cgagtgaaga aatgggagg aggctttgga   2400 ggcaaggaga cccggagcac tgtggtgtcc acggcagtgg ccctggctgc atataagacc   2460
```

```
ggccgccctg tgcgatgcat gctggaccgt gatgaggaca tgctgataac tggtggcaga    2520
catcccttcc tggccagata caaggttggc ttcatgaaga ctgggacagt tgtggctctt    2580
gaggtggacc acttcagcaa tgtggggaac acccaggatc tctctcagag tattatggaa    2640
cgagctttat tccacatgga caactgctat aaaatcccca acatccgggg cactgggcgg    2700
ctgtgcaaaa ccaaccttcc ctccaacacg gccttccggg gctttggggg gccccagggg    2760
atgctcattg ccgagtgctg gatgagtgaa gttgcagtga cctgtgggat gcctgcagag    2820
gaggtgcgga gaaaaaacct gtacaaagaa ggggacctga cacacttcaa ccagaagctt    2880
gagggtttca ccttgcccag atgctgggaa gaatgcctag caagctctca gtatcatgct    2940
cggaagagtg aggttgacaa gttcaacaag gagaattgtt ggaaaaagag aggattgtgc    3000
ataattccca ccaagtttgg aataagcttt acagttcctt ttctgaatca ggcaggagcc    3060
ctacttcatg tgtacacaga tggctctgtg ctgctgaccc acggggggac tgagatgggc    3120
caaggccttc ataccaaaat ggtccaggtg gccagtagag ctctgaaaat ccccaccctct   3180 aagatttata tcagcgagac aagcactaac actgtgccca cacctctccc cacggctgcc    3240
tctgtcagcg ctgacctcaa tggacaggcc gtctatgcgg cttgtcagac catcttgaaa    3300
aggctggaac cctacaagaa gaagaatccc agtggctcct gggaagactg ggtcacagct    3360
gcctacatgg acacagtgag cttgtctgcc actgggtttt atagaacacc caatctgggc    3420
tacagctttg agactaactc agggaacccc ttccactact tcagctatgg ggtggcttgc    3480
tctgaagtag aaatcgactg cctaacagga gatcataaga acctccgcac agatattgtc    3540
atggatgttg gctccagtct aaaccctgcc attgatattg acaggtggaa agggcatttt   3600
gtccagggcc ttggcctctt caccctagag gagctacact attccccccga ggggagcctg   3660 cacacccgtg gccctagcac ctacaagatc ccggcatttg gcagcatccc cattgagttc    3720
agggtgtccc tgctccgcga ctgccccaac aagaaggcca tctatgcatc gaaggctgtt    3780
ggagagccgc ccctcttcct ggctgcttct atcttctttg ccatcaaaga tgccatccgt    3840
gcagctcgag ctcagcacac aggtaataac gtgaaggaac tcttccggct agacagccct    3900
gccaccccgg agaagatccg caatgcctgc gtggacaagt tcaccaccct gtgtgtcact    3960
ggtgtcccag aaaactgcaa accctggtct gtgagggtct aa                       4002
```

<210> SEQ ID NO 9
<211> LENGTH: 2747
<212> TYPE: DNA
<213> ORGANISM: Homo sapiens
<220> FEATURE:
<223> OTHER INFORMATION: molybdenum cofactor sulfurase (MOCOS, MOS, HMCS), hypothetical protein FLJ20733 cDNA

<400> SEQUENCE: 9

```
gcctggatgg actagccggg gccatggccg gcgcggcggc ggagtcaggg cgggagctgt      60
ggaccttcgc gggttccccgg gacccgagcg caccgcggct agcctacggc tacggcccgg    120
gcagcctgcg cgagctgcgg gcgcgcgagt tcagccgcct gcaggaact gtctatcttg     180 accatgcagg tgccaccttg ttctcccaga gccagctcga aagcttcact agtgatctca    240
tggaaaacac ttatggtaat cctcacagcc agaacatcag cagcaagctc acccatgaca    300
ctgtggagca ggtgcgctac agaatcctgg cgcacttcca caccaccgca gaagactaca    360
ctgtgatctt cactgccggg agcacggctg ctctcaaact ggtggcagag gccttttccat    420 gggtgtccca gggcccagag agcagtggga gtcgcttctg ttacctcacc gacagccaca    480
```

```
cctccgtagt gggtatgcgg aacgtgacca tggctataaa tgtcatatcc accccggtca   540
ggccagagga cctgtggtct gcagaggaac gtagtgcttc agccagcaac ccagactgcc   600
agctgccgca tctcttctgc tacccagctc agagtaactt ttctggagtc ataccccc   660
tgtcctggat agaagaggtc aagtctgggc ggttgcaccc tgtgagcacg cctgggaagt   720
ggtttgtgct gctggatgca gcctcctacg tgagcacctc gcctttggac ctgtcagctc   780
accaggccga ctttgtcccc atctccttct ataagatctt cgggtttcct acaggcctgg   840
gcgctctgct ggtccataat cgtgcggctc ctctactgag gaagacctac tttggaggag   900
ggacagcctc tgcgtaccta gcaggagaag acttctacat cccgaggcag tcggtagctc   960
agaggtttga agatggcacc atctcattcc ttgatgttat cgcgctaaaa catggatttg  1020
acaccctaga gcgcctcaca ggtggaatgg agaatataaa gcagcacacc ttcaccttgg  1080
ctcagtatac ctacgtggcc ctgtcctctc tccagtaccc caatggagcc cctgtggtgc  1140
ggatttacag cgattctgag ttcagcagcc ctgaggttca gggcccaatc atcaatttta  1200
atgtgctgga tgacaaaggg aacatcattg ttactccca ggtggacaaa atggccagtc  1260
tttacaacat ccacctgcga actggctgct ctgtaacac tggggcctgc agaggcacc  1320
tgggcataag caacgagatg gtcaggaagc atttttcaggc tggtcatgtc tgtggggaca  1380
atatggacct catagatggg cagcccacag gatctgtgag gatttcattt ggatacatgt  1440
cgacgctgga tgatgtccag gcctttctta ggttcatcat agacactcgc ctgcactcat  1500
caggggactg gcctgtccct caggcccatg ctgacaccgg ggagactgga gccccatcag  1560
cagacagcca ggctgatgtt atacctgctg tcatgggcag acgtagcctc tcgcctcagg  1620
aagatgccct cacaggctcc agggtttgga caactcgtc tactgtgaat gctgtgcctg  1680
tggccccacc tgtgtgtgat gtcgccagaa cccagccgac tccttcagag aaagctgcag  1740
gagtcctgga gggggccctt gggccacatg ttgtcactaa cctttatctc tatccaatca  1800
aatcctgtgc tgcatttgag gtgaccaggt ggcctgtagg aaaccaaggg ctgctatatg  1860
accggagctg gatggttgtg aatcacaatg gtgtttgcct gagtcagaag caggaacccc  1920
ggctctgcct gatccagccc ttcatcgact tgcggcaaag gatcatggtc atcaaagcca  1980
aagggatgga gcctatagag gtgcctcttg aggaaaatag tgaacggact cagattcgcc  2040
aaaagcagggt ctgtgctgac agagtaagta cttatgattg tggagaaaaa atttcaagct  2100
ggttgtcaac atttttttgg cgtccttgtc atttgatcaa acaaagttca aactctcaaa  2160
ggaatgcaaa gaagaaacat ggaaaagatc aacttcctgg tacaatggcc acccttctc   2220
tggtgaatga ggcacagtat ctgctgatca acacatccag tattttggaa cttcaccggc  2280
aactaaacac cagtgatgag aatggaaagg aggaattatt ctcactgaag gatctcagct  2340
tgcgttttcg tgccaatatt attatcaatg gaaaagggc ttttgaagaa gagaaatggg  2400
atgagatttc aattggctct ttgcgtttcc aggttttggg gccttgtcac agatgccaga  2460
tgatttgcat cgaccagcaa actgggcaac gaaaccagca tgttttccaa aaactttctg  2520
agagtcgtga acaaaggtg aactttggca tgtacctgat gcatgcatca ttggatttat  2580
cctcccatg tttcctgtct gtaggatctc aggtgctccc tgtgttgaaa gagaatgtgg  2640
aaggtctcatga tttacctgca tctgagaaac caccaggatgt tacctcctaa aaaaatttt  2700
tagcataaag tttctctttt acagtgaaaa aaaaaaaaaa aaaaaaa     2747

<210> SEQ ID NO 10
<211> LENGTH: 2667
<212> TYPE: DNA
```

```
<213> ORGANISM: Homo sapiens
<220> FEATURE:
<223> OTHER INFORMATION: molybdenum cofactor sulfurase (MOCOS, MOS,
      HMCS), hypothetical protein FLJ20733 coding sequence (CDS)
<221> NAME/KEY: CDS
<222> LOCATION: (1)...(2667)
<223> OTHER INFORMATION: molybdenum cofactor sulfurase (MOCOS, MOS,
      HMCS), hypothetical protein FLJ20733

<400> SEQUENCE: 10
atggccggcg cggcggcgga gtcagggcgg gagctgtgga ccttcgcggg ttcccgggac      60
ccgagcgcac cgcggctagc ctacggctac ggcccgggca gcctgcgcga gctgcgggcg     120
cgcgagttca gccgcctggc aggaactgtc tatcttgacc atgcaggtgc caccttgttc     180
tcccagagcc agctcgaaag cttcactagt gatctcatgg aaaacactta tggtaatcct     240
cacagccaga acatcagcag caagctcacc catgacactg tggagcaggt gcgctacaga     300
atcctggcgc acttccacac caccgcagaa gactacactg tgatcttcac tgccgggagc     360
acggctgctc tcaaactggt ggcagaggcc tttccatggg tgtcccaggg cccagagagc     420
agtgggagtc gcttctgtta cctcaccgac agccacacct ccgtagtggg tatgcggaac     480
gtgaccatgg ctataaatgt catatccacc ccggtcaggc cagaggacct gtggtctgca     540
gaggaacgta gtgcttcagc cagcaaccca gactgccagc tgccgcatct cttctgctac     600
ccagctcaga gtaacttttc tggagtcaga taccccctgt cctggataga agaggtcaag     660
tctgggcggt tgcaccctgt gagcacgcct gggaagtggt tgtgctgct ggatgcagcc     720
tcctacgtga gcacctcgcc tttggacctg tcagctcacc aggccgactt tgtccccatc     780
tccttctata agatcttcgg gtttcctaca ggcctgggcg ctctgctggt ccataatcgt     840
gcggctcctc tactgaggaa gacctacttt ggaggaggga cagcctctgc gtacctagca     900
ggagaagact tctacatccc gaggcagtcg gtagctcaga ggtttgaaga tggcaccatc     960
tcattccttg atgttatcgc gctaaaacat ggatttgaca ccctagagcg cctcacaggt    1020
ggaatggaga atataaagca gcacaccttc accttggctc agtataccta cgtggccctg    1080
tcctctctcc agtaccccaa tggagcccct gtggtgcgga tttacagcga ttctgagttc    1140
agcagccctg aggttcaggg cccaatcatc aattttaatg tgctggatga caaagggaac    1200
atcattggtt actcccaggt ggacaaaatg gccagtcttt acaacatcca cctgcgaact    1260
ggctgcttct gtaacactgg ggcctgccag aggcacctgg gcataagcaa cgagatggtc    1320
aggaagcatt ttcaggctgg tcatgtctgt ggggacaata tggacctcat agatgggcag    1380
cccacaggat ctgtgaggat tcatttggat acatgtcgac gctggatga tgtccaggcc    1440
tttcttaggt tcatcataga cactcgcctg cactcatcag gggactggcc tgtccctcag    1500
gcccatgctg acaccgggga gactggagcc ccatcagcag acagccaggc tgatgttata    1560
cctgctgtca tgggcagacg tagcctctcg cctcaggaag atgccctcac aggctccagg    1620
gtttggaaca actcgtctac tgtgaatgct gtgcctgtgg ccccacctgt gtgtgatgtc    1680
gccagaaccc agccgactcc ttcagagaaa gctgcaggag tcctggaggg ggcccttggg    1740
ccacatgttg tcactaacct ttatctctat ccaatcaaat cctgtgctgc atttgaggtg    1800
accaggtggc ctgtaggaaa ccaagggctg ctatatgacc ggagctggat ggttgtgaat    1860
cacaatggtg tttgcctgag tcagaagcag gaaccccggc tctgcctgat ccagcccttc    1920
atcgacttgc ggcaaaggat catggtcatc aaagccaaag ggatggagcc tatagaggtg    1980
cctcttgagg aaaatagtga acggactcag attcgccaaa gcagggtctg tgctgacaga    2040
gtaagtactt atgattgtgg agaaaaaatt tcaagctggt tgtcaacatt ttttggccgt    2100
```

```
ccttgtcatt tgatcaaaca aagttcaaac tctcaaagga atgcaaagaa gaaacatgga    2160
aaagatcaac ttcctggtac aatggccacc ctttctctgg tgaatgaggc acagtatctg    2220
ctgatcaaca catccagtat tttggaactt caccggcaac taaacaccag tgatgagaat    2280
ggaaaggagg aattattctc actgaaggat ctcagcttgc gttttcgtgc aatattatt     2340 atcaatggaa aaagggcttt tgaagaagag aaatgggatg agatttcaat ggctctttg     2400 cgtttccagg ttttggggcc ttgtcacaga tgccagatga tttgcatcga ccagcaaact    2460
gggcaacgaa accagcatgt tttccaaaaa ctttctgaga gtcgtgaaac aaaggtgaac    2520
tttggcatgt acctgatgca tgcatcattg gatttatcct ccccatgttt cctgtctgta    2580
ggatctcagg tgctccctgt gttgaaagag aatgtggaag gtcatgattt acctgcatct    2640
gagaaacacc aggatgttac ctcctaa                                        2667
```

<210> SEQ ID NO 11
<211> LENGTH: 2667
<212> TYPE: DNA
<213> ORGANISM: Homo sapiens
<220> FEATURE:
<223> OTHER INFORMATION: molybdenum cofactor sulfurase (MOCOS, MOS, HMCS), hypothetical protein FLJ20733 2107C>A polymorphic site variant allele (exon 11)

<400> SEQUENCE: 11

```
atggccggcg cggcggcgga gtcagggcgg gagctgtgga ccttcgcggg ttcccgggac    60
ccgagcgcac cgcggctagc ctacggctac ggcccgggca gctgcgcga gctgcgggcg     120 cgcgagttca gccgcctggc aggaactgtc tatcttgacc atgcaggtgc caccttgttc    180
tcccagagcc agctcgaaag cttcactagt gatctcatgg aaaacactta tggtaatcct    240
cacagccaga acatcagcag caagctcacc catgacactg tggagcaggt gcgctacaga    300
atcctggcgc acttccacac caccgcagaa gactacactg tgatcttcac tgccgggagc    360
acggctgctc tcaaactggt ggcagaggcc tttccatggg tgtcccaggg cccagagagc    420
agtgggagtc gcttctgtta cctcaccgac agccacacct ccgtagtggg tatgcggaac    480
gtgaccatgg ctataaatgt catatccacc ccggtcaggc cagaggacct gtggtctgca    540
gaggaacgta tgcttcagc cagcaaccca gactgccagc tgccgcatct cttctgctac    600
ccagctcaga gtaactttc tggagtcaga taccccctgt cctggataga agaggtcaag    660
tctgggcggt tgcaccctgt gagcacgcct gggaagtggt tgtgctgct ggatgcagcc    720 tcctacgtga gcacctcgcc tttggacctg tcagctcacc aggccgactt tgtccccatc    780
tccttctata agatcttcgg gttccctaca ggcctgggcg ctctgctggt ccataatcgt    840
gcggctcctc tactgaggaa gacctacttt ggaggaggga cagcctctgc gtacctagca    900
ggagaagact tctacatccc gaggcagtcg gtagctcaga ggtttgaaga tggcaccatc    960
tcattccttg atgttatcgc gctaaaacat ggatttgaca ccctagagcg cctcacaggt    1020
ggaatggaga atataaagca gcacaccttc accttggctc agtataccta cgtggccctg    1080
tcctctctcc agtaccccaa tggagcccct gtggtgcgga tttacagcga ttctgagttc    1140
agcagccctg aggttcaggg cccaatcatc aattttaatg tgctggatga caaagggaac    1200
atcattggtt actcccaggt ggacaaaatg gccagtcttt acaacatcca cctgcgaact    1260
ggctgcttct gtaacactgg ggcctgccag aggcacctgg gcataagcaa cgagatggtc    1320
aggaagcatt tcaggctgg tcatgtctgt ggggacaata tggacctcat agatgggcag    1380
cccacaggat ctgtgaggat ttcatttgga tacatgtcga cgctggatga tgtccaggcc    1440
```

```
tttcttaggt tcatcataga cactcgcctg cactcatcag gggactggcc tgtccctcag      1500
gcccatgctg acaccgggga gactggagcc ccatcagcag acagccaggc tgatgttata      1560
cctgctgtca tgggcagacg tagcctctcg cctcaggaag atgccctcac aggctccagg      1620
gtttggaaca actcgtctac tgtgaatgct gtgcctgtgg ccccacctgt gtgtgatgtc      1680
gccagaaccc agccgactcc ttcagagaaa gctgcaggag tcctggaggg ggcccttggg      1740
ccacatgttg tcactaacct ttatctctat ccaatcaaat cctgtgctgc atttgaggtg      1800
accaggtggc ctgtaggaaa ccaagggctg ctatatgacc ggagctggat ggttgtgaat      1860
cacaatggtg tttgcctgag tcagaagcag gaaccccggc tctgcctgat ccagcccttc      1920
atcgacttgc ggcaaaggat catggtcatc aaagccaaag ggatggagcc tatagaggtg      1980
cctcttgagg aaaatagtga acggactcag attcgccaaa gcagggtctg tgctgacaga      2040
gtaagtactt atgattgtgg agaaaaaatt tcaagctggt tgtcaacatt ttttggccgt      2100
ccttgtaatt tgatcaaaca aagttcaaac tctcaaagga atgcaaagaa gaaacatgga      2160
aaagatcaac ttcctggtac aatggccacc ctttctctgg tgaatgaggc acagtatctg      2220
ctgatcaaca catccagtat tttggaactt caccggcaac taaacaccag tgatgagaat      2280
ggaaaggagg aattattctc actgaaggat ctcagcttgc gttttcgtgc caatattatt      2340
atcaatggaa aaagggcttt tgaagaagag aaatgggatg agatttcaat tggctctttg      2400
cgtttccagg ttttggggcc ttgtcacaga tgccagatga tttgcatcga ccagcaaact      2460
gggcaacgaa accagcatgt tttccaaaaa ctttctgaga gtcgtgaaac aaaggtgaac      2520
tttggcatgt acctgatgca tgcatcattg gatttatcct ccccatgttt cctgtctgta      2580
ggatctcagg tgctccctgt gttgaaagag aatgtggaag gtcatgattt acctgcatct      2640
gagaaacacc aggatgttac ctcctaa                                          2667

<210> SEQ ID NO 12
<211> LENGTH: 2667
<212> TYPE: DNA
<213> ORGANISM: Homo sapiens
<220> FEATURE:
<223> OTHER INFORMATION: MOLYBDENUM COFACTOR SULFURASE (MOCOS), 509C>T
      VARIANT ALLELE
<220> FEATURE:
<223> OTHER INFORMATION: molybdenum cofactor sulfurase (MOCOS, MOS,
      HMCS), hypothetical protein FLJ20733 509C>T polymorphic site
      variant allele (exon 4)

<400> SEQUENCE: 12
atggccggcg cggcggcgga gtcagggcgg gagctgtgga ccttcgcggg ttcccgggac        60
ccgagcgcac cgcggctagc ctacggctac ggcccgggca gcctgcgcga gctgcgggcg       120
cgcgagttca gccgcctggc aggaactgtc tatcttgacc atgcaggtgc caccttgttc       180
tcccagagcc agctcgaaag cttcactagt gatctcatgg aaaacactta tggtaatcct       240
cacagccaga acatcagcag caagctcacc catgacactg tggagcaggt gcgctacaga       300
atcctggcgc acttccacac caccgcagaa gactacactg tgatcttcac tgccgggagc       360
acggctgctc tcaaactggt ggcagaggcc tttccatggg tgtcccaggg cccagagagc       420
agtgggagtc gcttctgtta cctcaccgac agccacacct ccgtagtggg tatgcggaac       480
gtgaccatgg ctataaatgt catatccatc ccggtcaggc cagaggacct gtggtctgca       540
gaggaacgta gtgcttcagc cagcaaccca gactgccagc tgccgcatct cttctgctac       600
ccagctcaga gtaactttc tggagtcaga taccccctgt cctggataga agaggtcaag       660
```

```
tctgggcggt tgcaccctgt gagcacgcct gggaagtggt ttgtgctgct ggatgcagcc      720
tcctacgtga gcacctcgcc tttggacctg tcagctcacc aggccgactt tgtccccatc      780
tccttctata agatcttcgg gtttcctaca ggcctgggcg ctctgctggt ccataatcgt      840
gcggctcctc tactgaggaa gacctacttt ggaggaggga cagcctctgc gtacctagca      900
ggagaagact tctacatccc gaggcagtcg gtagctcaga ggtttgaaga tggcaccatc      960
tcattccttg atgttatcgc gctaaaacat ggatttgaca ccctagagcg cctcacaggt     1020
ggaatggaga atataaagca gcacaccttc accttggctc agtatacccta cgtggccctg     1080
tcctctctcc agtaccccaa tggagcccct gtggtgcgga tttacagcga ttctgagttc     1140
agcagccctg aggttcaggg cccaatcatc aattttaatg tgctggatga caaagggaac     1200
atcattggtt actcccaggt ggacaaaatg gccagtcttt acaacatcca cctgcgaact     1260
ggctgcttct gtaacactgg ggcctgccag aggcacctgg gcataagcaa cgagatggtc     1320
aggaagcatt tcaggctgg tcatgtctgt ggggacaata tggacctcat agatgggcag     1380
cccacaggat ctgtgaggat ttcatttgga tacatgtcga cgctggatga tgtccaggcc     1440
tttcttaggt tcatcataga cactcgcctg cactcatcag gggactggcc tgtccctcag     1500
gcccatgctg acaccgggga gactggagcc ccatcagcag acagccaggc tgatgttata     1560
cctgctgtca tgggcagacg tagcctctcg cctcaggaag atgccctcac aggctccagg     1620
gtttggaaca actcgtctac tgtgaatgct gtgcctgtgg ccccacctgt gtgtgatgtc     1680
gccagaaccc agccgactcc ttcagagaaa gctgcaggag tcctggaggg ggcccttggg     1740
ccacatgttg tcactaacct ttatctctat ccaatcaaat cctgtgctgc atttgaggtg     1800
accaggtggc ctgtaggaaa ccaagggctg ctatatgacc ggagctggat ggttgtgaat     1860
cacaatggtg tttgcctgag tcagaagcag gaaccccggc tctgcctgat ccagcccttc     1920
atcgacttgc ggcaaaggat catggtcatc aaagccaaag ggatggagcc tatagaggtg     1980
cctcttgagg aaaatagtga acggactcag attcgccaaa gcagggtctg tgctgacaga     2040
gtaagtactt atgattgtgg agaaaaaatt tcaagctggt tgtcaacatt ttttggccgt     2100
ccttgtcatt tgatcaaaca aagttcaaac tctcaaagga atgcaaagaa gaaacatgga     2160
aaagatcaac ttcctggtac aatggccacc ctttctctgg tgaatgaggc acagtatctg     2220
ctgatcaaca catccagtat tttggaactt caccggcaac taaacaccag tgatgagaat     2280
ggaaaggagg aattattctc actgaaggat ctcagcttgc gttttcgtgc caatattatt     2340
atcaatggaa aaagggcttt tgaagaagag aaatgggatg agatttcaat tggctctttg     2400
cgtttccagg ttttggggcc ttgtcacaga tgccagatga tttgcatcga ccagcaaact     2460
gggcaacgaa accagcatgt tttccaaaaa cttctctgaga gtcgtgaaac aaaggtgaac     2520
tttggcatgt acctgatgca tgcatcattg gatttatcct ccccatgttt cctgtctgta     2580
ggatctcagg tgctccctgt gttgaaagag aatgtggaag gtcatgattt acctgcatct     2640
gagaaacacc aggatgttac ctcctaa                                        2667
```

<210> SEQ ID NO 13
<211> LENGTH: 2667
<212> TYPE: DNA
<213> ORGANISM: Homo sapiens
<220> FEATURE:
<223> OTHER INFORMATION: molybdenum cofactor sulfurase (MOCOS, MOS, HMCS), hypothetical protein FLJ20733 1072G>A polymorphic site variant allele (exon 6)

<400> SEQUENCE: 13

```
atggccggcg cggcggcgga gtcagggcgg gagctgtgga ccttcgcggg ttcccgggac      60
ccgagcgcac cgcggctagc ctacggctac ggcccgggca gcctgcgcga gctgcgggcg     120
cgcgagttca gccgcctggc aggaactgtc tatcttgacc atgcaggtgc caccttgttc     180
tcccagagcc agctcgaaag cttcactagt gatctcatgg aaaacactta tggtaatcct     240
cacagccaga acatcagcag caagctcacc catgacactg tggagcaggt gcgctacaga     300
atcctggcgc acttccacac caccgcagaa gactacactg tgatcttcac tgccgggagc     360
acggctgctc tcaaactggt ggcagaggcc tttccatggg tgtcccaggg cccagagagc     420
agtgggagtc gcttctgtta cctcaccgac agccacacct ccgtagtggg tatgcggaac     480
gtgaccatgg ctataaatgt catatccacc ccggtcaggc cagaggacct gtggtctgca     540
gaggaacgta gtgcttcagc cagcaaccca gactgccagc tgccgcatct cttctgctac     600
ccagctcaga gtaactttc tggagtcaga tacccctgt cctggataga agaggtcaag     660
tctgggcggt tgcaccctgt gagcacgcct gggaagtggt tgtgctgct ggatgcagcc     720 tcctacgtga gcacctcgcc tttggacctg tcagctcacc aggccgactt tgtccccatc     780
tccttctata agatcttcgg gtttcctaca ggcctgggcg ctctgctggt ccataatcgt     840
gcggctcctc tactgaggaa gacctacttt ggaggaggga cagcctctgc gtacctagca     900
ggagaagact tctacatccc gaggcagtcg gtagctcaga ggtttgaaga tggcaccatc     960
tcattccttg atgttatcgc gctaaaacat ggatttgaca ccctagagcg cctcacaggt    1020
ggaatggaga atataaagca gcacaccttc accttggctc agtataccta catggccctg    1080
tcctctctcc agtaccccaa tggagcccct gtggtgcgga tttacagcga ttctgagttc    1140
agcagccctg aggttcaggg cccaatcatc aatttaatg tgctggatga caaagggaac    1200
atcattggtt actcccaggt ggacaaaatg gccagtcttt acaacatcca cctgcgaact    1260
ggctgcttct gtaacactgg ggcctgccag aggcacctgg gcataagcaa cgagatggtc    1320
aggaagcatt ttcaggctgg tcatgtctgt ggggacaata tggacctcat agatgggcag    1380
cccacaggat ctgtgaggat ttcatttgga tacatgtcga cgctggatga tgtccaggcc    1440
tttcttaggt tcatcataga cactcgcctg cactcatcag gggactggcc tgtccctcag    1500
gcccatgctg acaccgggga gactggagcc ccatcagcag acagccaggc tgatgttata    1560
cctgctgtca tgggcagacg tagcctctcg cctcaggaag atgccctcac aggctccagg    1620
gtttggaaca actcgtctac tgtgaatgct gtgcctgtgg ccccacctgt gtgtgatgtc    1680
gccagaaccc agccgactcc ttcagagaaa gctgcaggag tcctggaggg ggcccttggg    1740
ccacatgttg tcactaacct ttatctctat ccaatcaaat cctgtgctgc atttgaggtg    1800
accaggtggc ctgtaggaaa ccaagggctg ctatatgacc ggagctggat ggttgtgaat    1860
cacaatggtg tttgcctgag tcagaagcag gaaccccggc tctgcctgat ccagcccttc    1920
atcgacttgc ggcaaaggat catggtcatc aaagccaaag ggatggagcc tatagaggtg    1980
cctcttgagg aaaatagtga acggactcag attcgccaaa gcagggtctg tgctgacaga    2040
gtaagtactt atgattgtgg agaaaaaatt tcaagctggt tgtcaacatt ttttggccgt    2100
ccttgtcatt tgatcaaaca aagttcaaac tctcaaagga atgcaaagaa gaaacatgga    2160
aaagatcaac ttcctggtac aatggccacc ctttctctgg tgaatgaggc acagtatctg    2220
ctgatcaaca catccagtat tttggaactt caccggcaac taaacaccag tgatgagaat    2280
ggaaaggagg aattattctc actgaaggat ctcagcttgc gttttcgtgc caatattatt    2340
atcaatggaa aagggctttt tgaagaagag aaatgggatg agatttcaat tggctctttg    2400
```

```
cgtttccagg ttttggggcc ttgtcacaga tgccagatga tttgcatcga ccagcaaact   2460
gggcaacgaa accagcatgt tttccaaaaa ctttctgaga gtcgtgaaac aaaggtgaac   2520
tttggcatgt acctgatgca tgcatcattg gatttatcct ccccatgttt cctgtctgta   2580
ggatctcagg tgctccctgt gttgaaagag aatgtggaag gtcatgattt acctgcatct   2640
gagaaacacc aggatgttac ctcctaa                                       2667
```

<210> SEQ ID NO 14
<211> LENGTH: 2667
<212> TYPE: DNA
<213> ORGANISM: Homo sapiens
<220> FEATURE:
<223> OTHER INFORMATION: molybdenum cofactor sulfurase (MOCOS, MOS, HMCS), hypothetical protein FLJ20733 2600T>C polymorphic site variant allele (exon 15)

<400> SEQUENCE: 14

```
atggccggcg cggcggcgga gtcagggcgg gagctgtgga ccttcgcggg ttcccgggac     60
ccgagcgcac cgcggctagc ctacggctac ggcccgggca gcctgcgcga gctgcgggcg    120
cgcgagttca gccgcctggc aggaactgtc tatcttgacc atgcaggtgc caccttgttc    180
tcccagagcc agctcgaaag cttcactagt gatctcatgg aaaacactta tggtaatcct    240
cacagccaga acatcagcag caagctcacc catgacactg tggagcaggt gcgctacaga    300
atcctggcgc acttccacac caccgcagaa gactacactg tgatcttcac tgccgggagc    360
acggctgctc tcaaactggt ggcagaggcc tttccatggg tgtcccaggg cccagagagc    420
agtgggagtc gcttctgtta cctcaccgac agccacacct ccgtagtggg tatgcggaac    480
gtgaccatgg ctataaatgt catatccacc ccggtcaggc cagaggacct gtggtctgca    540
gaggaacgta gtgcttcagc cagcaacccca gactgccagc tgccgcatct cttctgctac    600
ccagctcaga gtaactttc tggagtcaga tacccctgt cctggataga agaggtcaag    660
tctgggcggt tgcaccctgt gagcacgcct gggaagtggt ttgtgctgct ggatgcagcc    720
tcctacgtga gcacctcgcc tttggacctg tcagctcacc aggccgactt tgtccccatc    780
tccttctata agatcttcgg gtttcctaca ggcctgggcg ctctgctggt ccataatcgt    840
gcggctcctc tactgaggaa gacctacttt ggaggaggga cagcctctgc gtacctagca    900
ggagaagact tctacatccc gaggcagtcg gtagctcaga ggtttgaaga tggcaccatc    960
tcattccttg atgttatcgc gctaaaacat ggatttgaca ccctagagcg cctcacaggt   1020
ggaatggaga atataaagca gcacaccttc accttggctc agtataccta cgtggccctg   1080
tcctctctcc agtaccccaa tggagcccct gtggtgcgga tttacagcga ttctgagttc   1140
agcagccctg aggttcaggg cccaatcatc aattttaatg tgctggatga caagggaac   1200 atcattggtt actcccaggt ggacaaaatg gccagtcttt acaacatcca cctgcgaact   1260
ggctgcttct gtaacactgg ggcctgccag aggcacctgg gcataagcaa cgagatggtc   1320
aggaagcatt ttcaggctgg tcatgtctgt ggggacaata tggacctcat agatgggcag   1380
cccacaggat ctgtgaggat ttcatttgga tacatgtcga cgctggatga tgtccaggcc   1440
tttcttaggt tcatcataga cactcgcctg cactcatcag gggactggcc tgtccctcag   1500
gcccatgctg acaccgggga gactggagcc ccatcagcag acagccaggc tgatgtttata   1560 cctgctgtca tgggcagacg tagcctctcg cctcaggaag atgccctcac aggctccagg   1620
gtttggaaca actcgtctac tgtgaatgct gtgcctgtgg ccccacctgt gtgtgatgtc   1680
gccagaaccc agccgactcc ttcagagaaa gctgcaggag tcctggaggg ggcccttggg   1740
```

-continued

```
ccacatgttg tcactaacct ttatctctat ccaatcaaat cctgtgctgc atttgaggtg    1800
accaggtggc ctgtaggaaa ccaagggctg ctatatgacc ggagctggat ggttgtgaat    1860
cacaatggtg tttgcctgag tcagaagcag gaaccccggc tctgcctgat ccagcccttc    1920
atcgacttgc ggcaaaggat catggtcatc aaagccaaag ggatggagcc tatagaggtg    1980
cctcttgagg aaaatagtga acggactcag attcgccaaa gcagggtctg tgctgacaga    2040
gtaagtactt atgattgtgg agaaaaaatt tcaagctggt tgtcaacatt ttttggccgt    2100
ccttgtcatt tgatcaaaca aagttcaaac tctcaaagga atgcaaagaa gaaacatgga    2160
aaagatcaac ttcctggtac aatggccacc ctttctctgg tgaatgaggc acagtatctg    2220
ctgatcaaca catccagtat tttggaactt caccggcaac taaacaccag tgatgagaat    2280
ggaaaggagg aattattctc actgaaggat ctcagcttgc gttttcgtgc caatattatt    2340
atcaatggaa aagggctttt tgaagaagag aaatgggatg agatttcaat tggctctttg    2400
cgtttccagg ttttggggcc ttgtcacaga tgccagatga tttgcatcga ccagcaaact    2460
gggcaacgaa accagcatgt tttccaaaaa ctttctgaga gtcgtgaaac aaaggtgaac    2520
tttggcatgt acctgatgca tgcatcattg gatttatcct ccccatgttt cctgtctgta    2580
ggatctcagg tgctccctgc gttgaaagag aatgtggaag gtcatgattt acctgcatct    2640
gagaaacacc aggatgttac ctcctaa                                       2667
```

<210> SEQ ID NO 15
<211> LENGTH: 2667
<212> TYPE: DNA
<213> ORGANISM: Homo sapiens
<220> FEATURE:
<223> OTHER INFORMATION: molybdenum cofactor sulfurase (MOCOS, MOS, HMCS), hypothetical protein FLJ20733 359G>A polymorphic site variant allele (exon 4)

<400> SEQUENCE: 15

```
atggccggcg cggcggcgga gtcagggcgg gagctgtgga ccttcgcggg ttcccgggac      60
ccgagcgcac cgcggctagc ctacggctac ggcccgggca gcctgcgcga gctgcgggcg     120
cgcgagttca gccgcctggc aggaactgtc tatcttgacc atgcaggtgc caccttgttc     180
tcccagagcc agctcgaaag cttcactagt gatctcatgg aaaacactta tggtaatcct     240
cacagccaga acatcagcag caagctcacc catgacactg tggagcaggt gcgctacaga     300
atcctggcgc acttccacac caccgcagaa gactacactg tgatcttcac tgccgggaac     360
acggctgctc tcaaactggt ggcagaggcc tttccatggg tgtcccaggg cccagagagc     420
agtgggagtc gcttctgtta cctcaccgac agccacacct ccgtagtggg tatgcggaac     480
gtgaccatgg ctataaatgt catatccacc ccggtcaggc cagaggacct gtggtctgca     540
gaggaacgta gtgcttcagc cagcaaccca gactgccagc tgccgcatct cttctgctac     600
ccagctcaga gtaactttc tggagtcaga taccccctgt cctggataga agaggtcaag     660
tctgggcggt tgcaccctgt gagcacgcct gggaagtggt ttgtgctgct ggatgcagcc     720
tcctacgtga gcacctcgcc tttgacctg tcagctcacc aggccgactt tgtccccatc     780
tccttctata agatcttcgg gtttcctaca ggcctgggcg ctctgctggt ccataatcgt     840
gcggctcctc tactgaggaa gacctacttt ggaggaggga cagcctctgc gtacctagca     900
ggagaagact tctacatccc gaggcagtcg gtagctcaga ggtttgaaga tggcaccatc     960
tcattccttg atgttatcgc gctaaaacat ggatttgaca ccctagagcg cctcacaggt    1020
ggaatggaga atataaagca gcacaccttc accttggctc agtataccta cgtggccctg    1080
```

-continued

```
tcctctctcc agtaccccaa tggagcccct gtggtgcgga tttacagcga ttctgagttc    1140
agcagccctg aggttcaggg cccaatcatc aattttaatg tgctggatga caaagggaac    1200
atcattggtt actcccaggt ggacaaaatg gccagtcttt acaacatcca cctgcgaact    1260
ggctgcttct gtaacactgg ggcctgccag aggcacctgg gcataagcaa cgagatggtc    1320
aggaagcatt ttcaggctgg tcatgtctgt ggggacaata tggacctcat agatgggcag    1380
cccacaggat ctgtgaggat ttcatttgga tacatgtcga cgctggatga tgtccaggcc    1440
tttcttaggt tcatcataga cactcgcctg cactcatcag gggactggcc tgtccctcag    1500
gcccatgctg acaccgggga gactggagcc catcagcag acagccaggc tgatgttata    1560
cctgctgtca tgggcagacg tagcctctcg cctcaggaag atgccctcac aggctccagg    1620
gtttggaaca actcgtctac tgtgaatgct gtgcctgtgg ccccacctgt gtgtgatgtc    1680
gccagaaccc agccgactcc ttcagagaaa gctgcaggag tcctggaggg ggcccttggg    1740
ccacatgttg tcactaacct ttatctctat ccaatcaaat cctgtgctgc atttgaggtg    1800
accaggtggc ctgtaggaaa ccaagggctg ctatatgacc ggagctggat ggttgtgaat    1860
cacaatggtg tttgcctgag tcagaagcag gaaccccggc tctgcctgat ccagcccttc    1920
atcgacttgc ggcaaaggat catggtcatc aaagccaaag ggatggagcc tatagaggtg    1980
cctcttgagg aaaatagtga acggactcag attcgccaaa gcagggtctg tgctgacaga    2040
gtaagtactt atgattgtgg agaaaaaatt tcaagctggt tgtcaacatt ttttggccgt    2100
ccttgtcatt tgatcaaaca aagttcaaac tctcaaagga atgcaaagaa gaaacatgga    2160
aaagatcaac ttcctggtac aatggccacc ctttctctgg tgaatgaggc acagtatctg    2220
ctgatcaaca catccagtat tttgaacctt caccggcaac taaacaccag tgatgagaat    2280
ggaaaggagg aattattctc actgaaggat ctcagcttgc gttttcgtgc aatatcatt    2340
atcaatggaa aaagggcttt tgaagaagag aaatgggatg agatttcaat tggctctttg    2400
cgtttccagg ttttggggcc ttgtcacaga tgccagatga tttgcatcga ccagcaaact    2460
gggcaacgaa accagcatgt tttccaaaaa cttttctgaga gtcgtgaaac aaaggtgaac    2520
tttggcatgt acctgatgca tgcatcattg gatttatcct ccccatgttt cctgtctgta    2580
ggatctcagg tgctccctgt gttgaaagag aatgtggaag gtcatgattt acctgcatct    2640
gagaaacacc aggatgttac ctcctaa                                        2667
```

<210> SEQ ID NO 16
<211> LENGTH: 4949
<212> TYPE: DNA
<213> ORGANISM: Homo sapiens
<220> FEATURE:
<223> OTHER INFORMATION: molybdenum hydroxylase aldehyde oxidase (AOX, AO), aldehyde oxidase 1 (AOX1, AOH1) cytosolic flavoenzyme subunit cDNA

<400> SEQUENCE: 16

```
cgccccactc ggcgggtcgg tgccgccggg tcccaggtgc ccgctacttc ccagaacctc      60
cgcctcccgc tccgggccct cgaaccagcg cggacaccac aatggaccgg cgtccgagc     120
tgctcttcta cgtgaacggc cgcaaggtga tagaaaaaaa tgtcgatcct gaaacaatgc     180
tgttgcctta tttgaggaag aagcttcgac tcacaggaac taagtatggc tgtggaggag     240
gaggctgtgg tgcttgtaca gtgatgatat cacgatacaa cccatcacc aagaggataa     300
ggcatcaccc agccaatgcc tgtctgattc ccatctgttc tctgtatggt gctgccgtca     360
ccacagtaga aggcatagga agcacccaca ccagaattca tcctgttcag gagaggattg     420
```

```
ccaagtgtca tggcacccag tgtggcttct gcacacctgg gatggtgatg tccatctaca    480
cgctgctcag gaaccaccca gagcccactc tggatcagtt aactgatgcc cttggtggta    540
acctgtgccg ttgcactgga tacaggccca taattgatgc atgcaagact ttctgtaaaa    600
cttcgggctg ctgtcaaagt aaagaaaatg gggtttgctg tttggatcaa ggaatcaatg    660
gattgccaga atttgaggaa ggaagtaaga caagtccaaa actcttcgca gaagaggagt    720
ttctgccatt ggatccaacc caggaactga tatttcctcc tgagctaatg ataatggctg    780
agaaacagtc gcaaaggacc agggtgtttg gcagtgagag aatgatgtgg ttttcccccg    840
tgaccctgaa ggaactgctg gaatttaaat tcaagtatcc ccaggctcct gttatcatgg    900
gaaacacctc tgtggggcct gaagtgaaat ttaaaggcgt ctttcaccca gttataattt    960
ctcctgatag aattgaagaa ctgagtgttg taaaccatgc atataatgga ctcacccttg   1020
gtgctggtct cagcctagcc caggtgaagg acattttggc tgatgtagtc cagaagcttc   1080
cagaggagaa gacacagatg taccatgctc tcctgaagca tttgggaact ctggctgggt   1140
cccagatcag gaacatggct tctttagggg gacacatcat tagcaggcat ccagattcag   1200
atctgaatcc catcctggct gtgggtaact gtacccctcaa cttgctatca aaagaaggaa   1260
aacgacagat tcctttaaat gagcaattcc tcagcaagtg ccctaatgca gatcttaagc   1320
ctcaagaaat cttggtctca gtgaacatcc cctactcaag gaagtgggaa tttgtgtcag   1380
ccttccgaca agcccagcga caggagaatg cgctagcgat agtcaattca ggaatgagag   1440 tctttttttgg agaaggggat ggcattatta gagagttatg catctcatat ggaggcgttg   1500
gtccagccac catctgtgcc aagaattcct gccagaaact cattggaagg cactggaacg   1560
aacagatgct ggatatagcc tgcaggctta ttctgaatga agtctccctt ttgggctcgg   1620
cgccaggtgg gaaagtggag ttcaagagga ctctcatcat cagcttcctc ttcaagttct   1680
acctggaagt gtcacagatt tgaaaaaga tggatccagt tcactatcct agccttgcag   1740
acaagtatga aagtgcttta gaagatcttc attccaaaca tcactgcagt acattaaagt   1800
accagaatat aggcccaaag cagcatcctg aagacccaat tggccacccc atcatgcatc   1860
tgtctggtgt gaagcatgcc acgggggagg ccatctactg tgatgacatg cctctggtgg   1920
accaggaact tttcttgact tttgtgacta gttcaagagc tcatgctaag attgtgtcta   1980
ttgatctgtc agaagctctc agcatgcccg gtgtggtgga catcatgaca gcagaacatc   2040
ttagtgacgt caactccttc tgctttttta ctgaagctga gaaatttctg cgacagata    2100 aggtgttctg tgtgggtcag cttgtctgtg ctgtgcttgc cgattctgag gttcaggcaa   2160
agcgagctgc taagcgagtg aagattgtct atcaagactt ggagccgctg atactaacaa   2220
ttgaggaaag tatacaacac aactcctcct tcaagccaga aaggaaactg aatatggaa    2280 atgttgacga agcatttaaa gtggttgatc aaattcttga aggtgaaata catatgggag   2340
gtcaagaaca ttttatatg gaaacccaaa gcatgcttgt cgttcccaag ggagaggatc    2400
aagaaatgga tgtctacgtg tccacacagt ttcccaaata tatacaggac attgttgcct   2460
caaccttgaa gctcccagct aacaaggtca tgtgccatgt aaggcgtgtt ggtgagcgt    2520 ttggagggaa ggtgttaaaa accggaatca ttgcagccgt cactgcattt gccgcaaaca   2580
aacatggccg tgcagttcgc tgtgttctgg aacgaggaga agacatgtta ataactggag   2640
gccgccatcc ttaccttgga aagtacaaag ctggattcat gaacgatggc agaatcttgg   2700
ccctggacat ggagcattac agcaatgcag gcgcctcctt ggatgaatca ttattcgtga   2760
tagaaatggg acttctgaaa atggacaatg cttacaagtt tcccaatctc cgctgccggg   2820
```

```
gttgggcatg cagaaccaac cttccatcca acacagcttt tcgtgggttt ggctttcctc    2880
aggcagcgct gatcaccgaa tcttgtatca cggaagttgc agccaaatgt ggactatccc    2940
ctgagaaggt gcgaatcata acatgtaca aggaaattga tcaaacaccc tacaaacaag    3000
agatcaatgc caagaaccta atccagtgtt ggagagaatg tatggccatg tcttcctact    3060
ccttgaggaa agttgctgtg aaaagttca atgcagagaa ttattggaag aagaaaggac    3120
tggccatggt ccccctgaag tttcctgttg gccttggctc acgtgctgct ggtcaggctg    3180
ctgccttggt tcacatttat cttgatggct ctgtgctggt cactcacggt ggaattgaaa    3240
tggggcaggg ggtccacact aaaatgattc aggtggtcag ccgtgaatta agaatgccaa    3300
tgtcgaatgt ccacctgcgt ggaacaagca cagaaactgt ccctaatgca aatatctctg    3360
gaggttctgt ggtggcagat ctcaacggtt tggcagtaaa ggatgcctgt caaactcttc    3420
taaaacgcct cgaacccatc atcagcaaga atcctaaagg aacttggaaa gactgggcac    3480
agactgcttt tgatgaaagc attaacctt cagctgttgg atacttcaga ggttatgagt    3540
cagacatgaa ctgggagaaa ggcgaaggcc agcccttcga atactttgtt tatggagctg    3600
cctgttccga ggttgaaata gactgcctga cggggatca taagaacatc agaacagaca    3660
ttgtcatgga tgttggctgc agtataaatc cagccattga cataggccag attgaaggtg    3720
catttattca aggcatggga ctttatacaa tagaggaact gaattattct ccccagggca    3780
ttctgcacac tcgtggtcca gaccaatata aaatccctgc catctgtgac atgcccacgg    3840
agttgcacat tgctttgttg cctccttctc aaaaactcaaa tactctttat tcatctaagg    3900
gtctgggaga gtcgggggtg ttcctggggt gttccgtgtt tttcgctatc catgacgcag    3960 tgagtcagc acgacaggag agaggcctgc atggacccct gacccttaat agtccactga    4020
ccccggagaa gattaggatg gcctgtgaag acaagttcac aaaaatgatt ccgagagatg    4080
aacctggatc ctacgttcct tggaatgtac ccatctgaat caaatgcaaa cttctggaga    4140
aaacagagtg cctcttccca gatggcaatc tgtcctatct ctgtgctgga agatgctaga    4200
tctgaaagac agagtttcca cagttcagaa atcatcccac agtgttgctt ttctatggag    4260
ctgatttaaa gtattccatt tagatttgat agatatgctt aagcaatcta taaatcattt    4320
tcaatgttat aaacactaat tggtttcctc tagggtgata ttcgtcatta ctctgtctct    4380
tcaatccatc cagctaaatg gaataggtga tgacttgcat gtgactccta cttggcttct    4440
atccaccaac agaaattata ccatatagtg aaaggcaatt ttctaaataa tttcattact    4500
aatatgaact gtgaagttgt cattttttca tttgtccttt tctgctatca ccttcctctt    4560
gtcagaatga atatagacac tgtatctaag tgggaccaaa gaaaaaatag cgaactttca    4620
ccaaagtttt catgaaaacc caaaagcttt aaaagttact atcaagaaat tgaaaggaaa    4680
cccacagaat aggataaaat atttgtaaat catatatttg ataaaagtct tgtaaccaga    4740
tacataaaga gctcttacaa ctcaataaaa ggcaagtaat ttaaaaatag gcaaaagaat    4800
tgctggatgg tatggtagtt ctattttag ttttttaccct aactactctg acttgatcat    4860
ttaacattct gtgtatgtaa caaaatatca catgcataaa tattatgtat caataaaatt    4920
ttttaatggg caaaaaaaaa aaaaaaaa                                       4949
```

<210> SEQ ID NO 17
<211> LENGTH: 4017
<212> TYPE: DNA
<213> ORGANISM: Homo sapiens
<220> FEATURE:
<223> OTHER INFORMATION: molybdenum hydroxylase aldehyde oxidase (AOX, AO), aldehyde oxidase 1 (AOX1, AOH1) cytosolic flavoenzyme subunit coding sequence (CDS)
<221> NAME/KEY: CDS
<222> LOCATION: (1)...(4017)
<223> OTHER INFORMATION: molybdenum hydroxylase aldehyde oxidase (AOX, AO), aldehyde oxidase 1 (AOX1, AOH1) cytosolic flavoenzyme subunit

<400> SEQUENCE: 17

| | | | | | |
|---|---|---|---|---|---|
| atggaccggg | cgtccgagct | gctcttctac | gtgaacggcc | gcaaggtgat | agaaaaaaat | 60 |
| gtcgatcctg | aaacaatgct | gttgccttat | ttgaggaaga | agcttcgact | cacaggaact | 120 |
| aagtatggct | gtggaggagg | aggctgtggt | gcttgtacag | tgatgatatc | acgatacaac | 180 |
| cccatcacca | agaggataag | gcatacccca | gccaatgcct | gtctgattcc | catctgttct | 240 |
| ctgtatggtg | ctgccgtcac | cacagtagaa | ggcataggaa | gcacccacac | cagaattcat | 300 |
| cctgttcagg | agaggattgc | caagtgtcat | ggcacccagt | gtggcttctg | cacacctggg | 360 |
| atggtgatgt | ccatctacac | gctgctcagg | aaccacccag | agcccactct | ggatcagtta | 420 |
| actgatgccc | ttggtggtaa | cctgtgccgt | tgcactggat | acaggcccat | aattgatgca | 480 |
| tgcaagactt | tctgtaaaac | ttcgggctgc | tgtcaaagta | agaaaatgg | ggtttgctgt | 540 |
| ttggatcaag | gaatcaatgg | attgccagaa | tttgaggaag | gaagtaagac | aagtccaaaa | 600 |
| ctcttcgcag | aagaggagtt | ctgccattg | gatccaaccc | aggaactgat | atttcctcct | 660 |
| gagctaatga | taatgctga | gaaacagtcg | caaaggacca | gggtgtttgg | cagtgagaga | 720 |
| atgatgtggt | tttccccccgt | gaccctgaag | gaactgctgg | aatttaaatt | caagtatccc | 780 |
| caggctcctg | ttatcatggg | aaacacctct | gtggggcctg | aagtgaaatt | taaaggcgtc | 840 |
| tttcacccag | ttataatttc | tcctgataga | attgaagaac | tgagtgttgt | aaaccatgca | 900 |
| tataatggac | tcacccttgg | tgctggtctc | agcctagccc | aggtgaagga | cattttggct | 960 |
| gatgtagtcc | agaagcttcc | agaggagaag | acacagatgt | accatgctct | cctgaagcat | 1020 |
| tgggaactc | tggctgggtc | ccagatcagg | aacatggctt | ctttaggggg | acacatcatt | 1080 |
| agcaggcatc | cagattcaga | tctgaatccc | atcctggctg | tgggtaactg | taccctcaac | 1140 |
| ttgctatcaa | aagaaggaaa | acgacagatt | cctttaaatg | agcaattcct | cagcaagtgc | 1200 |
| cctaatgcag | atcttaagcc | tcaagaaatc | ttggtctcag | tgaacatccc | ctactcaagg | 1260 |
| aagtgggaat | ttgtgtcagc | cttccgacaa | gcccagcgac | aggagaatgc | gctagcgata | 1320 |
| gtcaattcag | gaatgagagt | ctttttttgga | gaaggggatg | gcattattag | agagttatgc | 1380 |
| atctcatatg | gaggcgttgg | tccagccacc | atctgtgcca | agaattcctg | ccagaaactc | 1440 |
| attggaaggc | actggaacga | acagatgctg | gatatagcct | gcaggcttat | tctgaatgaa | 1500 |
| gtctcccttt | tgggctcggc | gccaggtggg | aaagtggagt | tcaagaggac | tctcatcatc | 1560 |
| agcttcctct | tcaagttcta | cctggaagtg | tcacagattt | tgaaaaagat | ggatccagtt | 1620 |
| cactatccta | gccttgcaga | caagtatgaa | agtgctttag | aagatcttca | ttccaaacat | 1680 |
| cactgcagta | cattaaagta | ccagaatata | ggcccaaagc | agcatcctga | agacccaatt | 1740 |
| ggccaccccca | tcatgcatct | gtctggtgtg | aagcatgcca | cgggggaggc | catctactgt | 1800 |
| gatgacatgc | ctctggtgga | ccaggaactt | ttcttgactt | ttgtgactag | ttcaagagct | 1860 |
| catgctaaga | ttgtgtctat | tgatctgtca | gaagctctca | gcatgccggg | tgtggtggac | 1920 |
| atcatgacag | cagaacatct | tagtgacgtc | aactccttct | gctttttac | tgaagctgag | 1980 |
| aaatttctgg | cgacagataa | ggtgttctgt | gtgggtcagc | ttgtctgtgc | tgtgcttgcc | 2040 |
| gattctgagg | ttcaggcaaa | gcgagctgct | aagcgagtga | agattgtcta | tcaagacttg | 2100 |
| gagccgctga | tactaacaat | tgaggaaagt | atacaacaca | actcctcctt | caagccagaa | 2160 |

```
aggaaactgg aatatggaaa tgttgacgaa gcatttaaag tggttgatca aattcttgaa    2220
ggtgaaatac atatgggagg tcaagaacat ttttatatgg aaacccaaag catgcttgtc    2280
gttcccaagg gagaggatca agaaatggat gtctacgtgt ccacacagtt tcccaaatat    2340
atacaggaca ttgttgcctc aaccttgaag ctcccagcta acaaggtcat gtgccatgta    2400
aggcgtgttg gtggagcgtt tggagggaag tgttaaaaaa ccggaatcat tgcagccgtc    2460
actgcatttg ccgcaaacaa acatggccgt gcagttcgct gtgttctgga acgaggagaa    2520
gacatgttaa taactggagg ccgccatcct taccttggaa agtacaaagc tggattcatg    2580
aacgatggca gaatcttggc cctggacatg gagcattaca gcaatgcagg cgcctccttg    2640
gatgaatcat tattcgtgat agaaatggga cttctgaaaa tggacaatgc ttacaagttt    2700
cccaatctcc gctgccgggg ttgggcatgc agaaccaacc ttccatccaa cacagctttt    2760
cgtgggtttg gctttcctca ggcagcgctg atcaccgaat cttgtatcac ggaagttgca    2820
gccaaatgtg gactatcccc tgagaaggtg cgaatcataa acatgtacaa ggaaattgat    2880
caaacaccct acaaacaaga gatcaatgcc aagaacctaa tccagtgttg gagagaatgt    2940
atggccatgt cttcctactc cttgaggaaa gttgctgtgg aaaagttcaa tgcagagaat    3000
tattggaaga agaaaggact ggccatggtc cccctgaagt ttcctgttgg ccttggctca    3060
cgtgctgctg gtcaggctgc tgccttggtt cacatttatc ttgatggctc tgtgctggtc    3120
actcacggtg gaattgaaat ggggcagggg gtccacacta aaatgattca ggtggtcagc    3180
cgtgaattaa gaatgccaat gtcgaatgtc cacctgcgtg gaacaagcac agaaactgtc    3240
cctaatgcaa atatctctgg aggttctgtg gtggcagatc tcaacggttt ggcagtaaag    3300
gatgcctgtc aaactcttct aaaacgcctc gaacccatca tcagcaagaa tcctaaagga    3360
acttggaaag actgggcaca gactgctttt gatgaaagca ttaacctttc agctgttgga    3420
tacttcagag gttatgagtc agacatgaac tgggagaaag gcgaaggcca gcccttcgaa    3480
tactttgttt atggagctgc ctgttccgag gttgaaatag actgcctgac ggggatcat    3540 aagaacatca aacagacat tgtcatggat gttggctgca gtataaatcc agccattgac    3600
ataggccaga ttgaaggtgc atttattcaa ggcatgggac tttatacaat agaggaactg    3660
aattattctc cccagggcat tctgcacact cgtggtccag accaatataa aatccctgcc    3720
atctgtgaca tgcccacgga gttgcacatt gctttgttgc ctccttctca aaactcaaat    3780
actctttatt catctaaggg tctgggagag tcggggtgt tcctggggtg ttccgtgttt    3840
ttcgctatcc atgacgcagt gagtgcagca cgacaggaga gaggcctgca tggacccttg    3900
acccttaata gtccactgac cccggagaag attaggatgg cctgtgaaga caagttcaca    3960
aaaatgattc cgagagatga acctggatcc tacgttcctt ggaatgtacc catctga       4017

<210> SEQ ID NO 18
<211> LENGTH: 4017
<212> TYPE: DNA
<213> ORGANISM: Homo sapiens
<220> FEATURE:
<223> OTHER INFORMATION: molybdenum hydroxylase aldehyde oxidase (AOX,
      AO), aldehyde oxidase 1 (AOX1, AOH1) cytosolic flavoenzyme
      subunit 3404A>G polymorphic site variant allele (exon 30)

<400> SEQUENCE: 18
atggaccggg cgtccgagct gctcttctac gtgaacggcc gcaaggtgat agaaaaaaat      60
gtcgatcctg aaacaatgct gttgccttat ttgaggaaga agcttcgact cacaggaact     120
aagtatggct gtggaggagg aggctgtggt gcttgtacag tgatgatatc acgatacaac     180
```

```
cccatcacca agaggataag gcatcaccca gccaatgcct gtctgattcc catctgttct      240
ctgtatggtg ctgccgtcac cacagtagaa ggcataggaa gcacccacac cagaattcat      300
cctgttcagg agaggattgc caagtgtcat ggcacccagt gtggcttctg cacacctggg      360
atggtgatgt ccatctacac gctgctcagg aaccacccag agcccactct ggatcagtta      420
actgatgccc ttggtggtaa cctgtgccgt tgcactggat acaggcccat aattgatgca      480
tgcaagactt tctgtaaaac ttcgggctgc tgtcaaagta agaaaatggg gtttgctgt       540 ttggatcaag gaatcaatgg attgccagaa tttgaggaag gaagtaagac aagtccaaaa      600
ctcttcgcag aagaggagtt tctgccattg gatccaaccc aggaactgat atttcctcct      660
gagctaatga taatggctga gaaacagtcg caaaggacca gggtgtttgg cagtgagaga      720
atgatgtggt tttcccccgt gaccctgaag gaactgctgg aatttaaatt caagtatccc      780
caggctcctg ttatcatggg aaacacctct gtggggcctg aagtgaaatt taaaggcgtc      840
tttcacccag ttataatttc tcctgataga attgaagaac tgagtgttgt aaaccatgca      900
tataatggac tcacccttgg tgctggtctc agcctagccc aggtgaagga cattttggct      960
gatgtagtcc agaagcttcc agaggagaag acacagatgt accatgctct cctgaagcat     1020
ttgggaactc tggctgggtc ccagatcagg aacatggctt ctttaggggg acacatcatt     1080
agcaggcatc cagattcaga tctgaatccc atcctggctg tgggtaactg taccctcaac     1140
ttgctatcaa agaaggaaa cgacagatt cctttaaatg agcaattcct cagcaagtgc      1200
cctaatgcag atcttaagcc tcaagaaatc ttggtctcag tgaacatccc ctactcaagg     1260
aagtgggaat ttgtgtcagc cttccgacaa gcccagcgac aggagaatgc gctagcgata     1320
gtcaattcag gaatgagagt cttttttgga gaagggatgg gcattattag agagttatgc     1380
atctcatatg gaggcgttgg tccagccacc atctgtgcca agaattcctg ccagaaactc     1440
attggaaggc actggaacga acagatgctg gatatagcct gcaggcttat tctgaatgaa     1500
gtctcccttt tgggctcggc gccaggtggg aaagtggagt tcaagaggac tctcatcatc     1560
agcttcctct tcaagttcta cctggaagtg tcacagattt tgaaaaagat ggatccagtt     1620
cactatccta gccttgcaga caagtatgaa agtgctttag aagatcttca ttccaaacat     1680
cactgcagta cattaaagta ccagaatata ggcccaaagc agcatcctga gacccaatt      1740 ggccacccca tcatgcatct gtctggtgtg aagcatgcca cggggggaggc catctactgt     1800 gatgacatgc ctctggtgga ccaggaactt ttcttgactt ttgtgactag ttcaagagct     1860
catgctaaga ttgtgtctat tgatctgtca gaagctctca gcatgccgg tgtggtggac     1920 atcatgacag cagaacatct tagtgacgtc aactccttct gctttttac tgaagctgag     1980 aaatttctgg cgacagataa ggtgttctgt gtgggtcagc ttgtctgtgc tgtgcttgcc     2040
gattctgagg ttcaggcaaa gcgagctgct aagcgagtga agattgtcta tcaagacttg     2100
gagccgctga tactaacaat tgaggaaagt atacaacaca actcctcctt caagccagaa     2160
aggaaactgg aatatggaaa tgttgacgaa gcatttaaag tggttgatca aattcttgaa     2220
ggtgaaatac atatgggagg tcaagaacat ttttatatgg aaacccaaag catgcttgtc     2280
gttcccaagg gagaggatca agaaatggat gtctacgtgt ccacacagtt tcccaaatat     2340
atacaggaca ttgttgcctc aaccttgaag ctcccagcta caaggtcat gtgccatgta     2400 aggcgtgttg gtggagcgtt tggagggaag gtgttaaaaa ccggaatcat gcagccgtc     2460 actgcatttg ccgcaaacaa acatggccgt gcagttcgct gtgttctgga acgaggagaa     2520
gacatgttaa taactggagg ccgccatcct taccttggaa agtacaaagc tggattcatg     2580
```

```
aacgatggca gaatcttggc cctggacatg gagcattaca gcaatgcagg cgcctccttg    2640
gatgaatcat tattcgtgat agaaatggga cttctgaaaa tggacaatgc ttacaagttt    2700
cccaatctcc gctgccgggg ttgggcatgc agaaccaacc ttccatccaa cacagctttt    2760
cgtgggtttg gctttcctca ggcagcgctg atcaccgaat cttgtatcac ggaagttgca    2820
gccaaatgtg gactatcccc tgagaaggtg cgaatcataa acatgtacaa ggaaattgat    2880
caaacaccct acaaacaaga gatcaatgcc aagaacctaa tccagtgttg gagagaatgt    2940
atggccatgt cttcctactc cttgaggaaa gttgctgtgg aaaagttcaa tgcagagaat    3000
tattggaaga agaaaggact ggccatggtc cccctgaagt ttcctgttgg ccttggctca    3060
cgtgctgctg gtcaggctgc tgccttggtt cacatttatc ttgatggctc tgtgctggtc    3120
actcacggtg gaattgaaat ggggcagggg gtccacacta aaatgattca ggtggtcagc    3180
cgtgaattaa gaatgccaat gtcgaatgtc cacctgcgtg gaacaagcac agaaactgtc    3240
cctaatgcaa atatctctgg aggttctgtg gtggcagatc tcaacggttt ggcagtaaag    3300
gatgcctgtc aaactcttct aaaacgcctc gaacccatca tcagcaagaa tcctaaagga    3360
acttggaaag actgggcaca gactgctttt gatgaaagca ttagcctttc agctgttgga    3420
tacttcagag gttatgagtc agacatgaac tgggagaaag gcgaaggcca gcccttcgaa    3480
tactttgttt atggagctgc ctgttccgag gttgaaatag actgcctgac gggggatcat    3540
aagaacatca gaacagacat tgtcatggat gttggctgca gtataaatcc agccattgac    3600
ataggccaga ttgaaggtgc atttattcaa ggcatgggac tttatacaat agaggaactg    3660
aattattctc cccagggcat tctgcacact cgtggtccag accaatataa aatccctgcc    3720
atctgtgaca tgcccacgga gttgcacatt gctttgttgc ctccttctca aaactcaaat    3780
actctttatt catctaaggg tctgggagag tcgggggtgt tcctggggtg ttccgtgttt    3840
ttcgctatcc atgacgcagt gagtgcagca cgacaggaga gaggcctgca tggacccttg    3900
acccttaata gtccactgac cccggagaag attaggatgg cctgtgaaga caagttcaca    3960
aaaatgattc cgagagatga acctggatcc tacgttcctt ggaatgtacc catctga      4017
```